(12) United States Patent
Riebel et al.

(10) Patent No.: US 6,271,178 B1
(45) Date of Patent: Aug. 7, 2001

(54) SUBSTITUTED 2,4-DIAMINO-1,3,5-TRIAZINE AS HERBICIDE

(75) Inventors: Hans-Jochem Riebel, Wuppertal; Stefan Lehr, Leverkusen; Uwe Stelzer, Burscheid, all of (DE); Yukiyoshi Watanabe, Oyama (JP); Markus Dollinger, Overland Park, KS (US); Toshio Goto, Kokubunji-machi (JP)

(73) Assignees: Bayer AG, Leverkusen (DE); Nihon Bayer Agrochem K.K., Tokyo (JP)

( * ) Notice: Subject to any disclaimer, the term of this patent is extended or adjusted under 35 U.S.C. 154(b) by 0 days.

(21) Appl. No.: 09/284,089

(22) PCT Filed: Sep. 29, 1997

(86) PCT No.: PCT/EP97/05319

§ 371 Date: Apr. 7, 1999

§ 102(e) Date: Apr. 7, 1999

(87) PCT Pub. No.: WO98/15538

PCT Pub. Date: Apr. 16, 1998

(30) Foreign Application Priority Data

Oct. 10, 1996 (DE) ............................................... 196 41 694

(51) Int. Cl.$^7$ ..................... C07D 251/52; C07D 251/18; A01N 43/70
(52) U.S. Cl. ..................... 504/232; 504/230; 504/233; 504/234; 544/206; 544/207; 544/208; 544/209; 544/210
(58) Field of Search ..................... 544/204, 205, 544/206, 207, 208, 209, 210; 504/230, 232, 233, 234

(56) References Cited

U.S. PATENT DOCUMENTS

| 3,816,419 | 6/1974 | Cross et al. ..................... 260/249.9 |
| 3,932,167 | 1/1976 | Cross et al. ..................... 71/93 |
| 5,286,905 | 2/1994 | Nakamura et al. ..................... 564/234 |
| 5,290,754 | 3/1994 | Nishii et al. ..................... 504/232 |
| 5,403,815 | 4/1995 | Nishii et al. ..................... 504/230 |
| 5,728,876 | 3/1998 | Balkenhohl et al. ..................... 564/136 |

FOREIGN PATENT DOCUMENTS

| 3426919 | 1/1986 | (DE) . |
| 4000610 | 7/1991 | (DE) . |
| 196 41 693 | 4/1998 | (DE) . |
| 0 191 496 | 8/1986 | (EP) . |
| 273328 | 6/1988 | (EP) . |
| 300313 | 1/1989 | (EP) . |
| 0 320 898 | 6/1989 | (EP) . |
| 411153 | 6/1991 | (EP) . |
| WO 9700254 | 3/1997 | (WO) . |
| WO 9708156 | 6/1997 | (WO) . |

OTHER PUBLICATIONS

Tetrahedron: Asymmetry, vol. 5, No. 5, (month unavailable) 1994, pp. 817–820, Calmes et al, Assymetric Supported Reactions: Synthesis of Chiral Amines.

Tetrahedron Letters, vol. 29, No. 2, pp. 223–224, 1988, Sakito et al, Aysmmetric Reduction of Oxime Ethers. Distinction of Anti and Syn Isomers Leading to Enantiomeric Amines.

Tetrahedron Letters, vol. 36, No. 22, pp. 3917–3920, 1995, Willems et al, Asymmetric Imine Isomerisation in the Enantioselective Synthesis of Chiral Amines from Prochiral Ketones.

*Primary Examiner*—John M. Ford
(74) *Attorney, Agent, or Firm*—Joseph C. Gil

(57) ABSTRACT

The invention relates to novel substituted 2,4-diamino-1,3, 5-triazines of the formula (I)

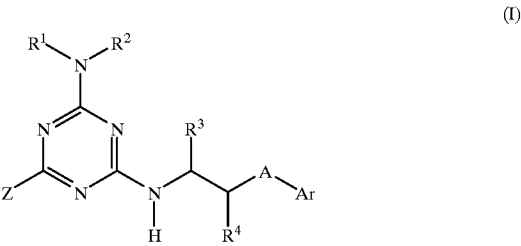

In which
$R^1$ represents hydrogen or optionally substitued alkyl,
$R^2$ represents formyl or represents in each case optionally substituted alkylcarbonyl, alkoxycarbonyl, alkylsulphonyl, arylcarbonyl or arylsulphonyl,
$R^3$ represents in each case optionally substituted alkyl or cycloalkyl,
$R^4$ represents hydrogen or alkyl,
A represents oxygen or methylene,
Ar represents in each case optionally substituted aryl or heterocyclyl, and
z represents hydrogen, hydroxyl, cyano, nitrogen, halogen or represents in each case optionally substituted alkyl, alkoxy, alkylcarbonyl, alkoxycarbonyl, alkylthio, alkylsulphinyl, alkylsulphonyl, alkenyl or alkinyl,
(except for three prior-art compounds),
to processes and to novel intermediates for preparation of the novel compounds and to their use as herbicides.

4 Claims, No Drawings

SUBSTITUTED 2,4-DIAMINO-1,3,5-TRIAZINE AS HERBICIDE

TECHNICAL FIELD OF THE INVENTION

The invention relates to novel substituted 2,4-diamino-1,3,5-triazines, to processes and to novel intermediates for their preparation and to their use as herbicides.

BACKGROUND OF THE INVENTION

A number of substituted 2,4-diamino-triazines is already known from the (patent) literature (cf. U.S. Pat. No. 3,816,419, U.S. 3,932,167, EP 191496, EP 273328, EP 411153/ WO 90/09378, WO 97/00254, WO 97/08156). However, these compounds have hitherto not attained any particular importance.

DETAILED DESCRIPTION OF THE INVENTION

This invention, accordingly, provides the novel substituted 2,4-diamino-1,3,5-triazines of the general formula (I)

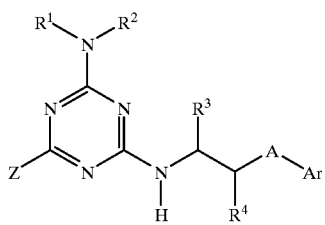

(I)

in which $R^1$ represents hydrogen or optionally substituted alkyl,
$R^2$ represents formyl or represents in each case optionally substituted alkylcarbonyl, alkoxycarbonyl, alkylsulphonyl, arylcarbonyl or arylsulphonyl,
$R^3$ represents in each case optionally substituted alkyl or cycloalkyl,
$R^4$ represents hydrogen or alkyl,
A represents oxygen or methylene,
Ar represents in each case optionally substituted aryl or heterocyclyl, and
Z represents hydrogen, hydroxyl, cyano, nitrogen, halogen or represents in each case optionally substituted alkyl, alkoxy, alkylcarbonyl, alkoxycarbonyl, alkylthio, alkylsulphinyl, alkylsulphonyl, alkenyl or alinyl, but excluding the compounds 2-formylamino-4-[1-methyl-3-(3ethoxy-phenyl)-propylamino]-6-(1-fluoro-1-methyl-ethyl)-1,3,5-triazine, 2-formylamino-4-[1-methyl-3-(2-cyano-phenyl)-propylamino]-6-(1,1,2,2-tetrafluoro-ethyl)-1,3,5-triazine and 2-formylamino-4-[1-methyl-3-(4-iodophenyl)-propylamino]-6(2-chloro-ethyl)-1,3,5-triazine.

(which have already been disclosed in WO 97/08156).

The novel 2,4-diamino-1,3,Striazines of the general formula (I) are obtained when (a) 2,4-diamino-1,3,5-triazines of the general formula (11)

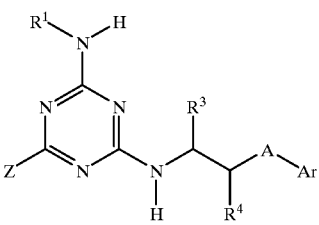

(II)

in which
$R^1$, $R^3$, $R^4$, A, Ar and Z are each as defined above
are reacted with acylating or sulphonylating agents of the general formula (III)

$$Y-R^2 \quad (III)$$

in which
$R^2$ is as defined above and
Y represents halogen, alkoxy or —O—$R^2$,
if appropriate in the presence of a reaction auxiliary and if appropriate in the presence of a diluent,
or when (b) to prepare compounds of the formula (I), except for those where Z=$NO_2$, substituted biguanidines of the general formula (IV)

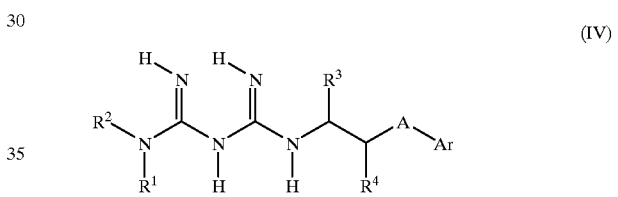

(IV)

in which
$R^1$, $R^2$, $R^3$, $R^4$, A and Ar are each as defined above
and/or acid adducts of compounds of the general formula (IV)
are reacted with alkoxycarbonyl compounds of the general formula (V)

$$Z-CO-OR' \quad (V)$$

in which
Z, with the exception of nitro, is as defined above and
R represents alkyl,
if appropriate in the presence of a reaction auxiliary and if appropriate in the presence of a diluent,
or when
(c) substituted triazines of the general formula (VI)

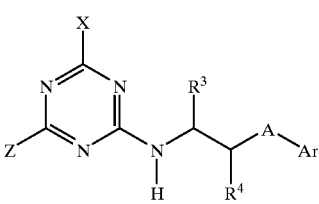

(VI)

in which
$R^3$, $R^4$, A, Ar and Z are each as defined above and
x represents halogen or alkoxy are reacted with nitrogen compounds of the general formula (VII)

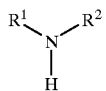
(VII)

in which
R¹ and R² are each as defined above,
if appropriate in the presence of a reaction auxiliary and if appropriate in the presence of a diluent,
and, if appropriate, further conversions within the scope of the above definition of substituents are carried out by customary methods on the compounds of the general formula (I) obtained by the processes described under (a), (b) or (c).

The novel substituted 2,4-diamino-1,3,5-triazines of the general formula (I) have strong and selective herbicidal activity.

The compounds of the general formula (I) according to the invention contain at least one asymmetrically substituted carbon atom and can therefore be present in different enantiomeric (R- and S-configured forms) or diastereomeric forms. The invention relates both to the different possible individual enantiomeric or stereoisomeric forms of the compounds of the general formula (I), and to the mixtures of these isomeric compounds.

In the definitions, the hydrocarbon chains, such as alkyl—also in combination with heteroatoms, such as in alkoxy or alkylthio—are in each case straight-chain or branched.

Halogen generally represents fluorine, chlorine, bromine or iodine, preferably represents fluorine, chlorine or bromine, and in particular represents fluorine or chlorine.

The invention preferably provides compounds of the formula (I) in which
R¹ represents hydrogen or represents optionally cyano-, halogen- or C₁–C₄-alkoxy-substituted alkyl having 1 to 6 carbon atoms,
R² represents formyl, represents in each case optionally cyano-, halogen- or C₁–C₄-alkoxy-substituted alkylcarbonyl, alkoxycarbonyl or alkylsulphonyl having in each case 1 to 6 carbon atoms in the alkyl groups, or represents in each case optionally cyano-, halogen-, C₁–C₄-alkyl-, halogeno-C₁–C₄-alkyl-, C₁–C₄-alkoxy-, halogeno-C₁–C₄-alkoxy- or C₁–C₄-alkoxy-carbonyl-substituted phenylcarbonyl, naphthylcarbonyl, phenylsulphonyl or naphthylsulphonyl,
R³ represents optionally hydroxyl-, cyano-, halogen- or C₁–C₄-alkoxy-substituted alkyl having 1 to 6 carbon atoms or represents optionally cyano-, halogen- or C₁–C₄-alkyl-substituted cycloalkyl having 3 to 6 carbon atoms,
R⁴ represents hydrogen or alkyl having 1 to 4 carbon atoms,
A represents oxygen or methylene,
Ar represents in each case optionally substituted phenyl, naphthyl or heterocyclyl,
where the possible heterocyclyl radicals are preferably selected from the group below:
furyl, benzofuryl, dihydrobenzofuryl, tetrahydrofuryl, thienyl, benzothienyl, thiazolyl, benzothiazolyl, oxazolyl, benzoxazolyl, thiadiazolyl, oxadiazolyl, pyrazolyl, pyrrolyl, indolyl, pyridinyl, quinolinyl, isoquinolinyl and pyrimidinyl,
and where the possible substituents are in each case preferably selected from the group below:
hydroxyl, cyano, nitro, halogen, in each case optionally hydroxyl-, cyano- or halogen-substituted alkyl or alkoxy having in each case 1 to 6 carbon atoms, in each case optionally halogen-substituted alkylcarbonyl, alkoxycarbonyl, alkylthio, alkylsulphinyl or alkylsulphonyl having in each case 1 to 6 carbon atoms in the alkyl groups, in each case optionally hydroxyl-, cyano-, nitro-, halogen-, C₁–C₄-alkyl, C₁–C₄-halogenoalkyl-, C₁–C₄-alkoxy- or C₁–C₄-halogenoalkoxy-substituted phenyl or phenoxy, and also in each case optionally halogen-substituted methylenedioxy or ethylenedioxy, and
Z represents hydrogen, represents halogen, represents in each case optionally hydroxyl-, cyano-, nitro-, halogen-, C₁–C₄-alkoxy-, C₁–C₄-alkyl-carbonyl-, C₁–C₄-alkoxy-carbonyl-, C₁–C₄-alkylthio-, C₁–C₄-alkylsulphinyl- or C₁–C₄-alkylsulphonyl-substituted alkyl, alkoxy, alkylcarbonyl, alkoxycarbonyl, alkylthio, alkylsulphinyl or alkylsulphonyl having in each case 1 to 6 carbon atoms in the alkyl groups, or represents in each case optionally halogen- or C₁–C₄-alkoxy-substituted alkenyl or alkinyl having in each case 2 to 6 carbon atoms,
but excluding the compounds
2-formylamino-4-[1-methyl-3-(3-ethoxy-phenyl)-propylamino]-6-(1-fluoro-1-methyl-ethyl)-1,3,5-triazine, 2-formylamino-4-[1-methyl-3-(2-cyano-phenyl)-propylamino]-6-(1,1,2,2-tetrafluoro-ethyl)-1,3,5-triazine and 2-formylamino-4-[1-methyl-3-(4-iodo-phenyl)-propylamino]-6(2-chloro-ethyl)-1,3,5-triazine.
(which have already been disclosed in WO 97/08156).

From among the compounds of the formula (I) defined above as preferred ("preferably"), particular emphasis is given to the following groups:
(A) the compounds of the formula (I) in which A, R¹, R², R³, R⁴ and Z are each as defined above and Ar represents in each case optionally substituted phenyl or naphthyl, the possible substituents being as defined above;
(B) the compounds of the formula (1) in which A, R¹, R², R³, R⁴ and Z are each as defined above and Ar represents in each case optionally substituted heterocyclyl, the possible heterocyclyl groupings and the possible substituents being as defined above.

The invention in particular relates to compounds of the formula (I) in which
R¹ represents hydrogen or represents in each case optionally hydroxyl-, cyano-, fluorine-, chlorine-, methoxy- or ethoxy-substituted methyl, ethyl, n- or i-propyl, n-, i-, s- or t-butyl,
R² represents in each case optionally cyano-, fluorine-, chlorine-, bromine-, methoxy- or ethoxy-substituted acetyl, propionyl, n- or i-butyroyl, methoxycarbonyl, ethoxycarbonyl, methylsulphonyl, ethylsulphonyl, n- or i-propylsulphonyl, n-, i-, s- or t-butylsulphonyl, or represents in each case optionally cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-, methoxycarbonyl- or ethoxycarbonyl-substituted phenylcarbonyl or phenylsulphonyl,
R³ represents in each case optionally hydroxyl-, cyano-, fluorine-, chlorine-, methoxy- or ethoxy-substituted methyl, ethyl, n- or i-propyl, n-, i-, s- or t-butyl or represents in each case optionally cyano-, fluorine-, chlorine-, methyl- or ethyl-substituted cyclopropyl, cyclobutyl, cyclopentyl or cyclohexyl,
R⁴ represents hydrogen or methyl,
A represents oxygen or methylene,
Ar represents in each case optionally substituted phenyl, naphthyl or heterocyclyl, where the possible heterocyclyl radicals are preferably selected from the group below:
furyl, benzofuryl, dihydrobenzofuryl, tetrahydrofuryl, thienyl, benzothienyl, thiazolyl, benzothiazolyl, oxazolyl, benzoxazolyl, thiadiazolyl, oxadiazolyl, pyrazolyl, pyrrolyl, indolyl, pyridinyl, quinolinyl, isoquinolinyl and pyrimidinyl,
and where the possible substituents are in each case preferably selected from the group below:
hydroxyl, cyano, nitro, fluorine, chlorine, bromine, in each case optionally hydroxyl-cyano-, fluorine- or chlorine-substituted methyl, ethyl, n- or i-propyl, n-, i-, s- or t-butyl, methoxy, ethoxy, n- or i-propoxy, n-, i-, s- or t-butoxy, in each case optionally fluorine- or chlorine-substituted acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, in each case optionally hydroxyl-, cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl or phenoxy, and also in each case optionally fluorine- or chlorine-substituted methylenedioxy or ethylenedioxy, and
Z represents hydrogen, fluorine, chlorine, bromine, represents in each case optionally hydroxyl-, cyano-, nitro-, fluorine-, chlorine-, methoxy-, ethoxy-, n- or i-propoxy-, n-, i-, s- or t-butoxy-, methylthio-ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents in each case optionally fluorine-, chlorine-, bromine-, methoxy- or ethoxy-substituted ethenyl, propenyl, butenyl, ethinyl, propinyl or butinyl.

From among the compounds of the formula (I) defined above as being particularly preferred, particular emphasis is given to the following groups:
(AA) the compounds of the formula (I) in which A, $R^1$, $R^2$, $R^3$, $R^4$ and Z are each as defined above and Ar represents in each case optionally substituted phenyl or naphthyl, the possible substituents being as defined above, with the proviso that the substituents of the carbon atom to which $R^3$ is attached are arranged in the R configuration;
(BB) the compounds of the formula (I) in which A, $R^1$, $R^2$, $R^3$, $R^4$ and Z are each as defined above and Ar represents in each case optionally substituted phenyl or naphthyl, the possible substituents being as defined above, with the proviso that the substituents of the carbon atom to which $R^3$ is attached are arranged in the S configuration;
(CC) the compounds of the formula (1) in which A, $R^1$, $R^2$, $R^3$, $R^4$ and Z are each as defined above and Ar represents in each case optionally substituted furyl, thienyl, pyridinyl or pyrimidinyl, the possible substituents being as defined above, with the proviso that these compounds are present as racemic mixtures;
(DD) the compounds of the formula (I) in which A, $R^1$, $R^2$, $R^3$, $R^4$ and Z are each as defined above and Ar represents in each case optionally substituted furyl, thienyl, pyridinyl or pyrimidinyl, the possible substituents being as defined above, with the proviso that the substituents of the carbon atom to which $R^3$ is attached are arranged in the R configuration;
(EE) the compounds of the formula (I), in which A, $R^1$, $R^2$, $R^3$, $R^4$ and Z are each as defined above and Ar represents in each case optionally substituted furyl, thienyl, pyridinyl or pyrimidinyl, the possible substituents being as defined above, with the proviso that the substituents of the carbon atom to which $R^3$ is attached are arranged in the S configuration;

The abovementioned general or preferred radical definitions apply both to the end products of the formula (I) and also, correspondingly, to the starting materials or intermediates required in each case for the preparation. These radical definitions can be combined with each other at will, i.e. including combinations between the abovementioned preferred ranges.

Examples of the compounds of the formula (1) according to the invention are listed in the groups below. The general formulae here represent in each case the R enantiomers, the S enantiomers and the racemates.

Group 1

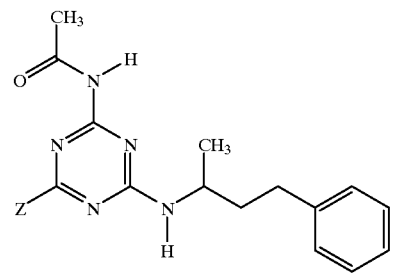

(I-1)

Here, Z has, for example, the meanings given below:
Hydrogen, methyl, ethyl, n- or i-propyl, n-, i-, s- or t-butyl, fluoromethyl, difluoromethyl, trifluoromethyl, chloromethyl, dichloromethyl, chlorofluoromethyl, chlorobromomethyl, chlorodifluoromethyl, fluorodichloromethyl, bromodifluoromethyl, trichloromethyl, 1-fluoro-ethyl, 2-fluoro-ethyl, 1-chloro-ethyl, 2-chloro-ethyl, 1-chloro-1-fluoroethyl, 1-fluoro-propyl, 2-fluoro-propyl, 3-fluoro-propyl, 1-fluoro-1-methyl-ethyl, 2-fluoro-1-methyl-ethyl, 1-chloro-1-methyl-ethyl, 1-fluoro-1-methyl-propyl, 1-chloro-1-ethyl-propyl, 1-fluoro-1-ethyl-propyl, 1-chloro-1-ethyl-propyl, 1-fluoro-2-methyl-propyl, 1-chloro-2-methyl-propyl, 1-chloro-propyl, 2-chloro-propyl, 3-chloro-propyl, 1-chloro -methyl-ethyl, 2-chloro-1-methyl-ethyl, 1,1-difluoro-ethyl, 1,2-difluoro-ethyl, 1,1-dichloro-ethyl, 2,2,2-trifluoro-ethyl, 1,2,2,2-tetrafluoro-ethyl, perfluoroethyl, 1,1-difluoro-propyl, 1,1-dichloro-propyl, perfluoropropyl, 1-fluoro-butyl, 1-chloro-butyl, perfluoropentyl, perfluorohexyl, 1-hydroxyl-ethyl, acetyl, 1,1-bis-acetyl-methyl, 1-acetyl-1-methoxycarbonyl-methyl, 1-acetyl-1-ethoxycarbonyl-methyl, methoxymethyl, 1,1-dimethoxy-methyl, 1-methoxy-ethyl, 2-methoxy-ethyl, 1,1-dimethoxy-ethyl, ethoxymethyl, 1-ethoxyethyl, 2-ethoxy-ethyl, 2-methoxy-1- methyl-ethyl, 2-methoxy-1-ethyl-ethyl, 2-ethoxy-1-methyl-ethyl, 2-ethoxy-1-ethyl-ethyl, methylthiomethyl, ethylthiomethyl, 1-methylthio-ethyl, 2-methylthioethyl, 1-ethylthio-ethyl, 2-ethylthioethyl, methylsulphinylmethyl, ethylsulphinylmethyl, methylsulphonylmethyl, ethylsulphonylmethyl, methoxy, ethoxy, n- or i-propoxy, methylthio, ethylthio, n- or i-propylthio, methylsulphinyl, ethylsulphinyl, methylsulphonyl, ethylsulphonyl, fluoromethoxy, difluoromethoxy, trifluoromethoxy, fluoroethoxy, difluoroethoxy, trifluoroethoxy, difluoromethylthio, trifluoromethylthio, vinyl, 1-chloro-vinyl, 2-chloro-vinyl, 1-fluoro-vinyl, 2-fluoro-vinyl, 1-bromo-vinyl, 2-bromo-vinyl, 1,2-dichloro-vinyl, 1,2-dibromo-vinyl, 1,2-difluoro-vinyl, 2,2-dichloro-vinyl, 2,2-difluoro-vinyl, 2,2-dibromo-vinyl, 1-chloro-2-fluoro-vinyl, 2-bromo-2-chloro-vinyl, trichlorovinyl, methoxyvinyl, ethoxyvinyl, allyl, 2-chloro-allyl, 3-chloro-allyl, 3,3-dichloro-allyl, 1-propenyl, isopropenyl, 1-chloro-2-propenyl, 1-fluoro-2-propenyl, 1-bromo-2-propenyl, 1,2-dichloro-1-propenyl, 1,2-dibromo-1-propenyl, 1,2-difluoro-1-propenyl, 1,1-dichloro-2-propenyl, 1,1-dibromo-2-propenyl, 1,I-difluoro-2-propenyl, 1,1,3,3,3-pentafluoro-2-propenyl, 2-buten-1-yl, 2-buten-2-yl, 3chloro-2-butenyl, 3-bromo-2-butenyl, 3,3,3-trifluoro-2-butenyl, ethinyl, 2-chloro-ethinyl, 2-bromo-ethinyl, 1-propinyl, 2-propinyl, 3,3,3-trifluoro-1-propinyl.

Group 2

(I-2)

Here, Z has, for example, the meanings given above in group 1.

Group 3

(I-3)

Here, Z has, for example, the meanings given above in group 1.

Group 4

(I-4)

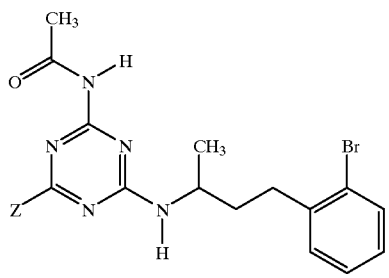

Here, Z has, for example, the meanings given above in group 1.

Group 5

(1-5)

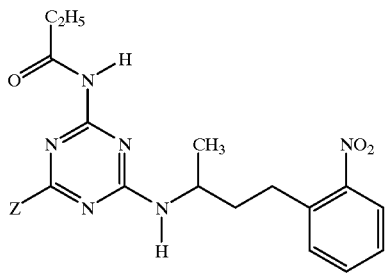

Here, Z has, for example, the meanings given above in group 1.

Group 6

(I-6)

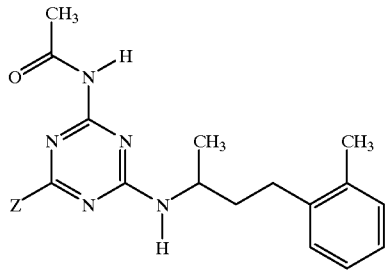

Here, Z has, for example, the meanings given above in group 1.

Group 7

(1-7)

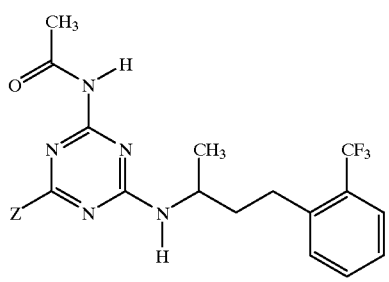

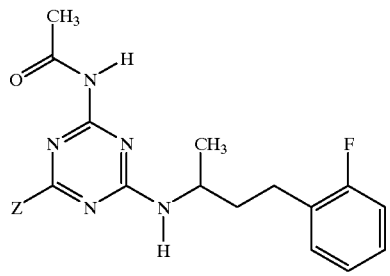

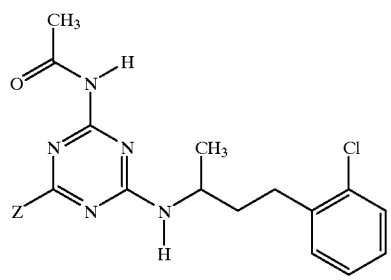

Group 8

(I-8)

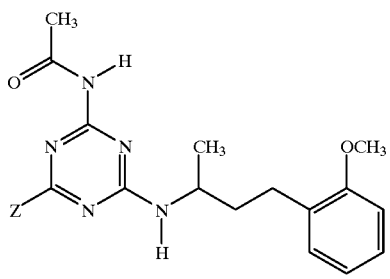

Here, Z has, for example, the meanings given above in group 1.

Group 9

(I-9)

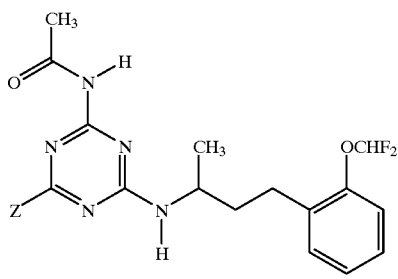

Here, Z has, for example, the meanings given above in group 1.

Group 10

(I-10)

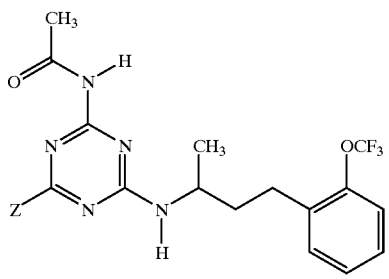

Here, Z has, for example, the meanings given above in group 1.

Group 11

(I-11)

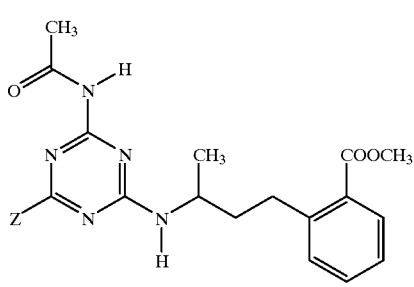

Here, Z has, for example, the meanings given above in group 1.

Group 12

(I-12)

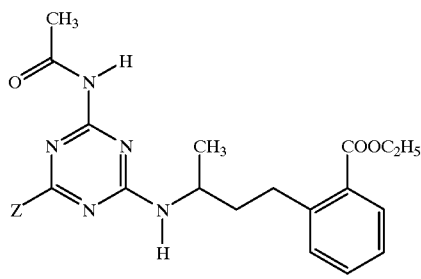

Here, Z has, for example, the meanings given above in group 1.

Group 13

(I-13)

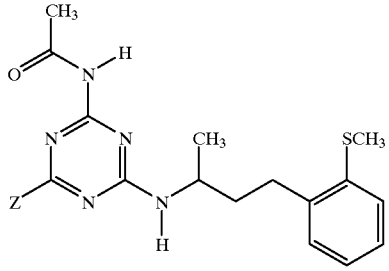

Here, Z has, for example, the meanings given above in group 1.

Group 14

(I-14)

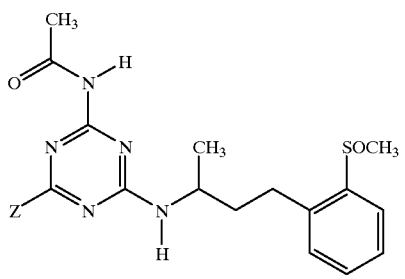

Here, Z has, for example, the meanings given above in group 1.

Group 15

(I-15)

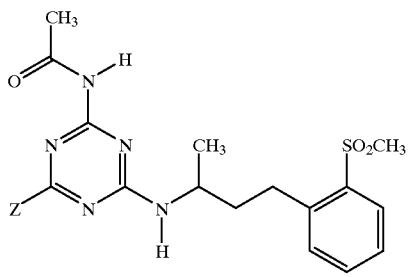

Here, Z has, for example, the meanings given above in group 1.

Group 16

(I-16)

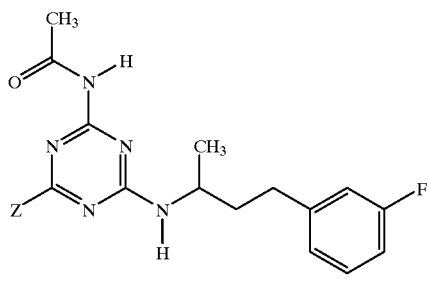

Here, Z has, for example, the meanings given above in group 1.

Group 17

(I-17)

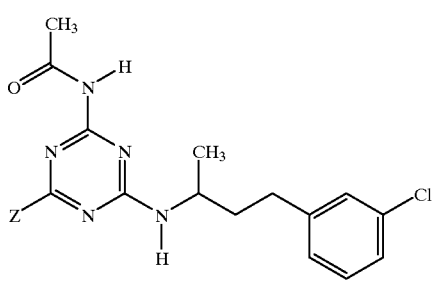

Here, Z has, for example, the meanings given above in group 1.

Group 18

(I-18)

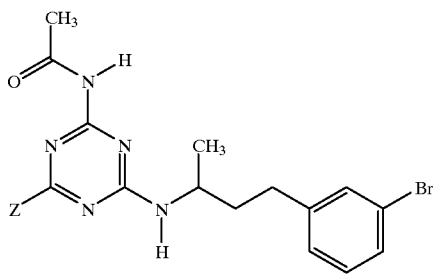

Here, Z has, for example, the meanings given above in group 1.

Group 19

(I-19)

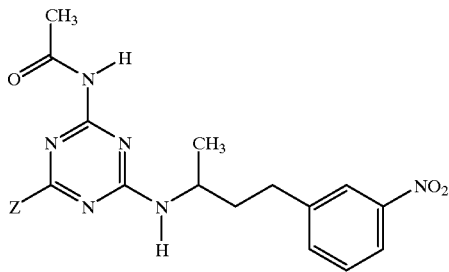

Here, Z has, for example, the meanings given above in group 1.

Group 20

(I-20)

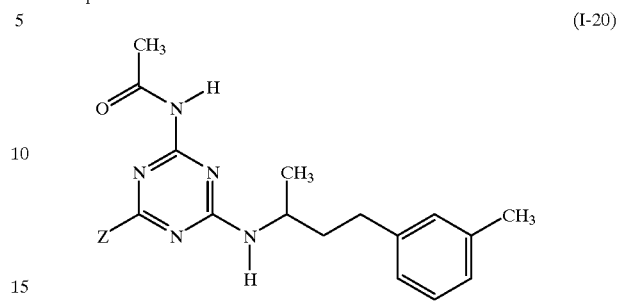

Here, Z has, for example, the meanings given above in group 1.

Group 21

(I-21)

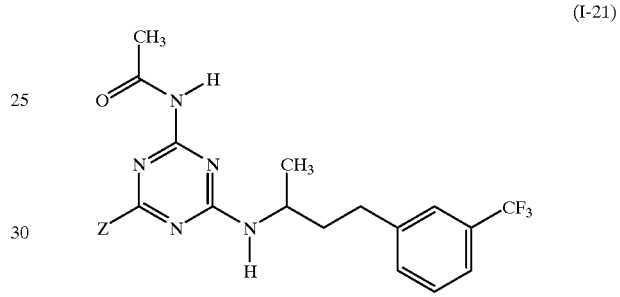

Here, Z has, for example, the meanings given above in group 1.

Group 22

(I-22)

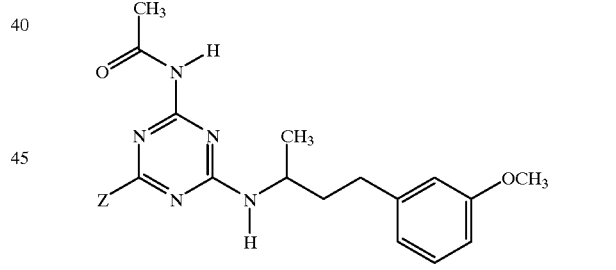

Here, Z has, for example, the meanings given above in group 1.

Group 23

(I-23)

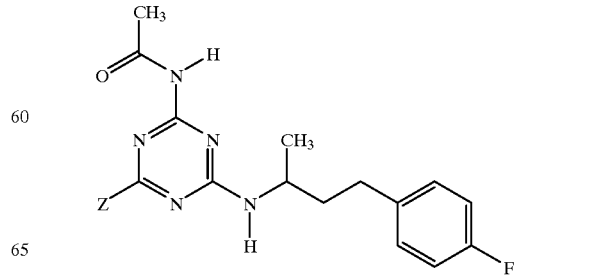

Here, Z has, for example, the meanings given above in group 1.

Group 24

(I-24)

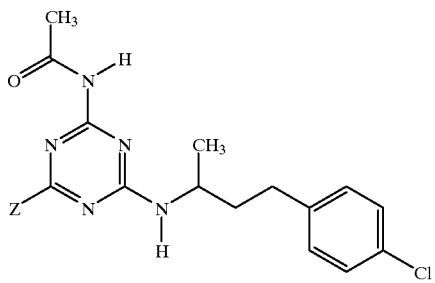

Here, Z has, for example, the meanings given above in group 1.

Group 25

(I-25)

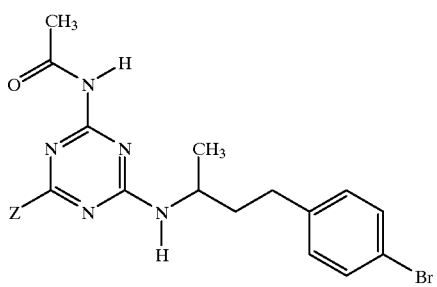

Here, Z has, for example, the meanings given above in group 1.

Group 26

(I-26)

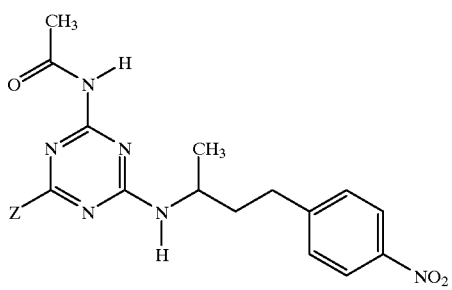

Here, Z has, for example, the meanings given above in group 1.

Group 27

(I-27)

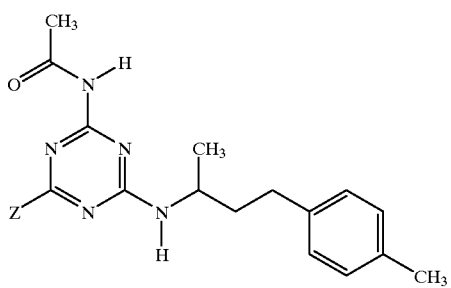

Here, Z has, for example, the meanings given above in group 1.

Group 28

(I-28)

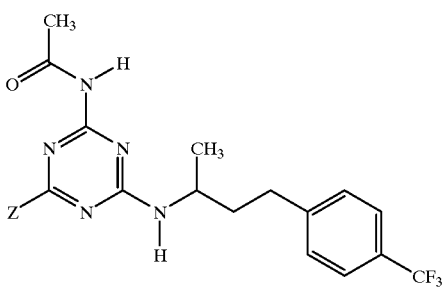

Here, Z has, for example, the meanings given above in group 1.

Group 29

(I-29)

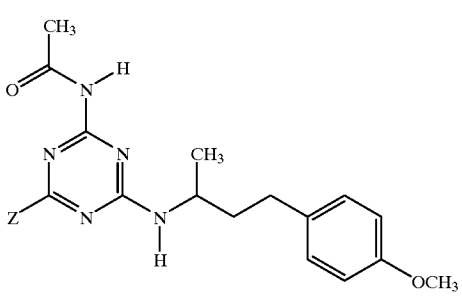

Here, Z has, for example, the meanings given above in group 1.

Group 30

(I-30)

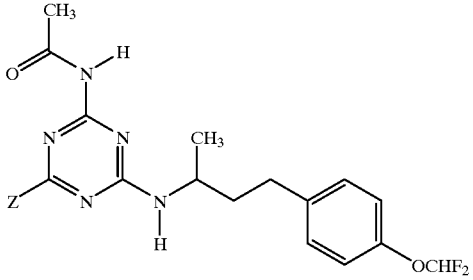

Here, Z has, for example, the meanings given above in group 1.

Group 31

(I-31)

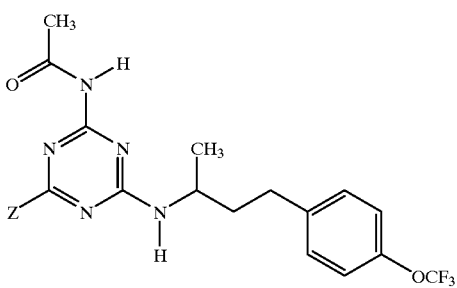

Here, Z has, for example, the meanings given above in group 1.

Group 32

(I-32)

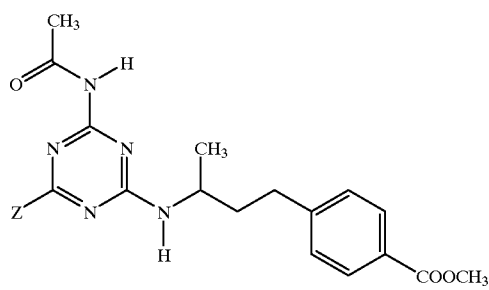

Here, Z has, for example, the meanings given above in group 1.

Group 33

(I-33)

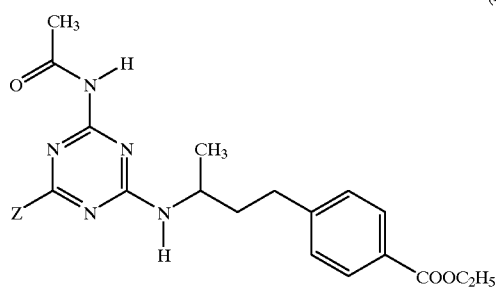

Group 34

(I-34)

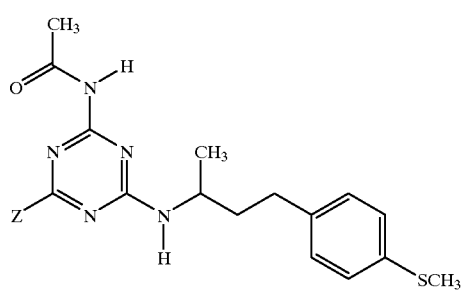

Here, Z has, for example, the meanings given above in group 1.

Group 35

(I-35)

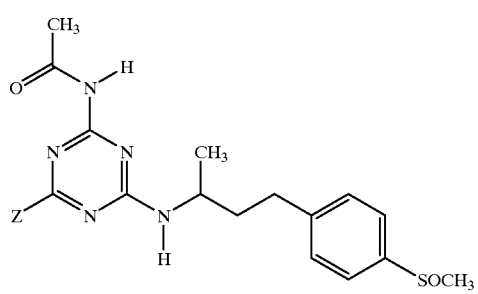

Here, Z has, for example, the meanings given above in group 1.

Group 36

(I-36)

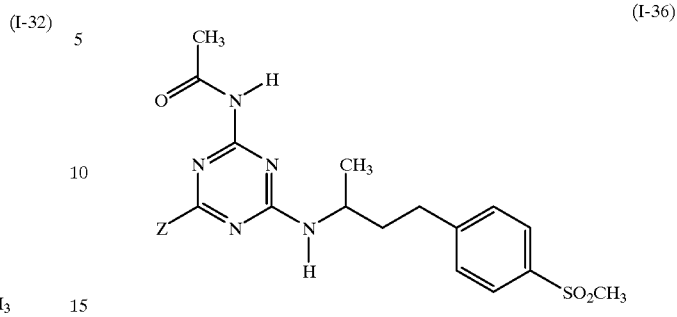

Here, Z has, for example, the meanings given above in group 1.

Group 37

(I-37)

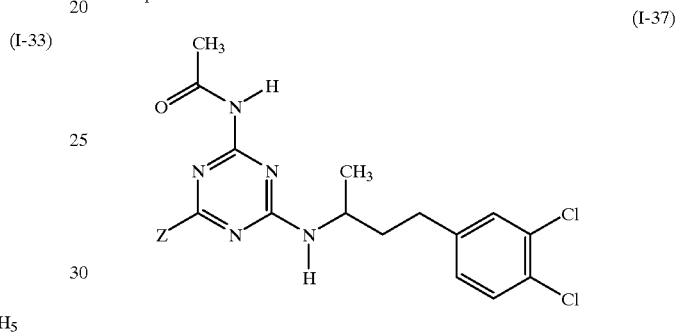

Here, Z has, for example, the meanings given above in group 1.

Group 38

(I-38)

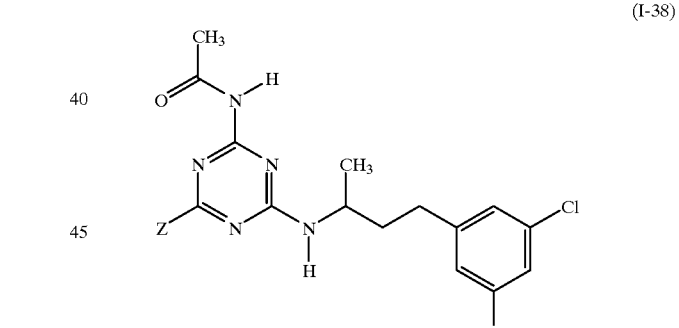

Here, Z has, for example, the meanings given above in group 1.

Group 39

(I-39)

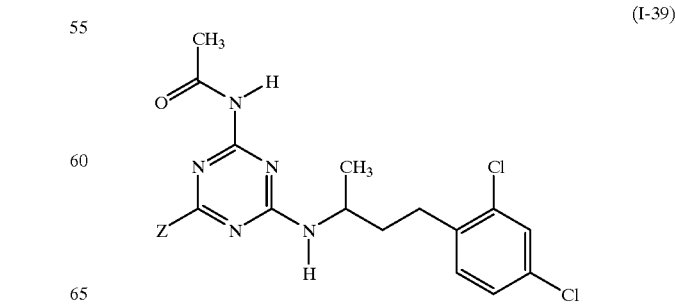

Here, Z has, for example, the meanings given above in group 1.

Group 40 (I-40)

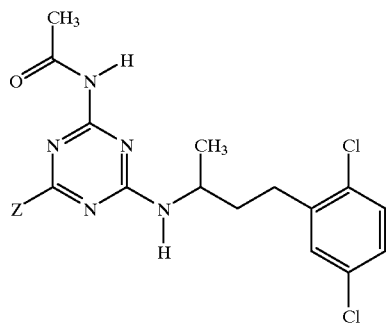

Here, Z has, for example, the meanings given above in group 1.

Group 41 (I-41)

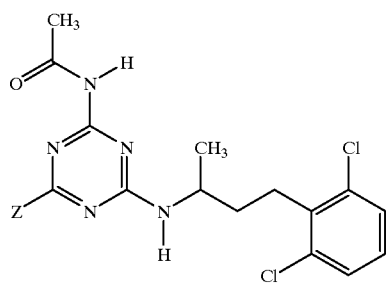

Here, Z has, for example, the meanings given above in group 1.

Group 42 (I-42)

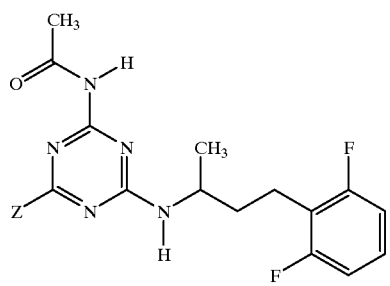

Here, Z has, for example, the meanings given above in group 1.

Group 43 (I-43)

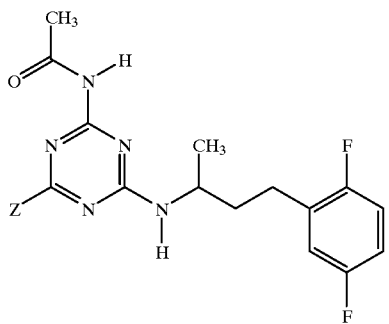

Here, Z has, for example, the meanings given above in group 1.

Group 44 (I-44)

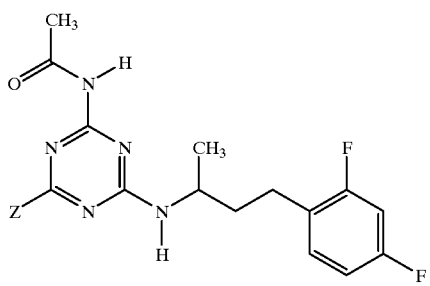

Here, Z has, for example, the meanings given above in group 1.

Group 45 (I-45)

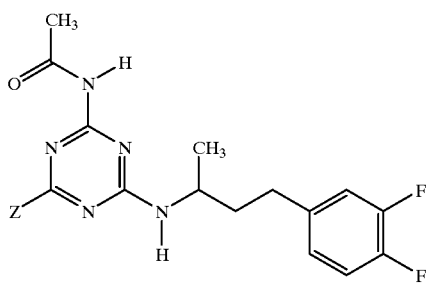

Group 46
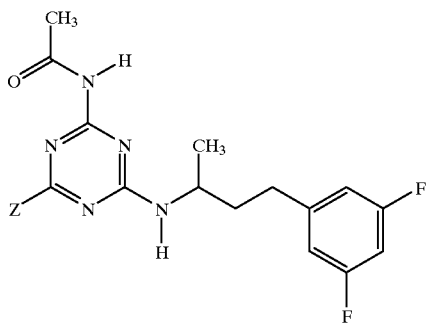
(I-46)
Here, Z has, for example, the meanings given above in group 1.
Group 47
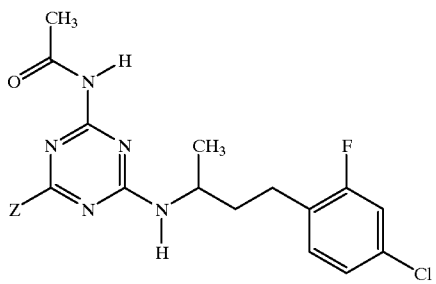
(I-47)
Here, Z has, for example, the meanings given above in group 1.
Group 48
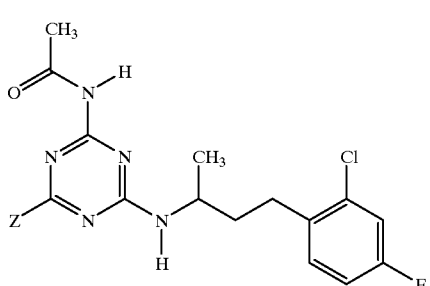
(I-48)
Group 49
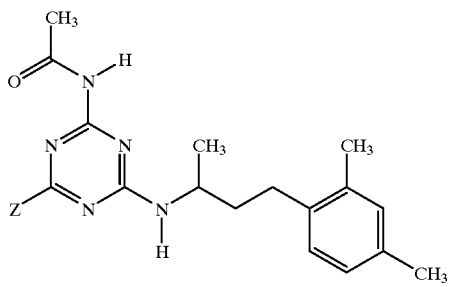
(I-49)
Here, Z has, for example, the meanings given above in group 1.
Group 50
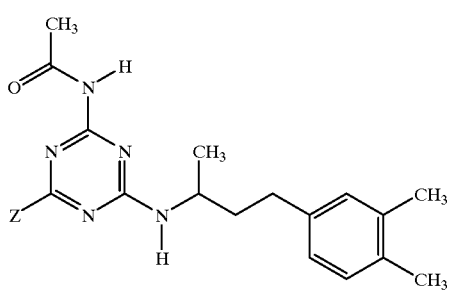
(I-50)
Here, Z has, for example, the meanings given above in group 1.
Group 51
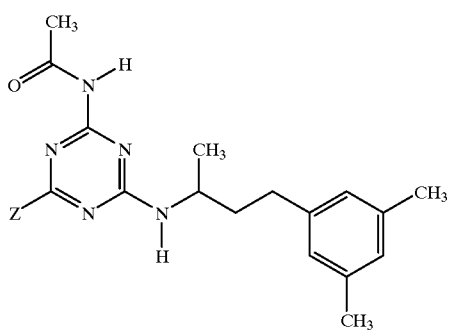
(I-51)

Group 52
(I-52)
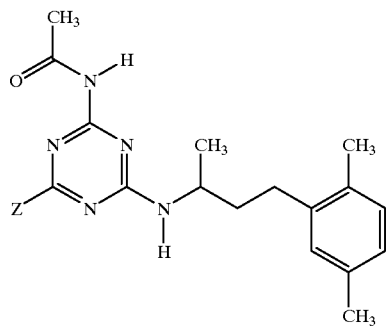
Here, Z has, for example, the meanings given above in group 1.
Group 53
(I-53)
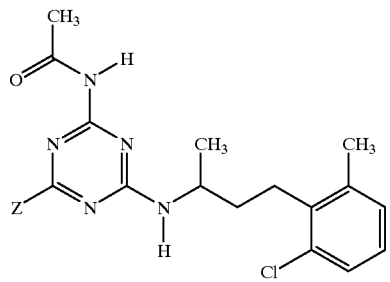
Here, Z has, for example, the meanings given above in group 1.
Group 54
(I-54)
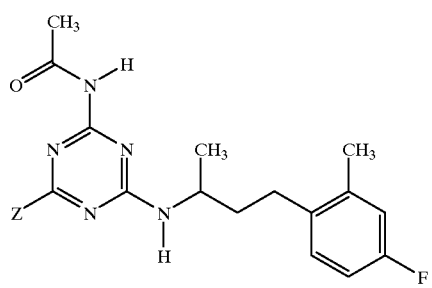
Here, Z has, for example, the meanings given above in group 1.
Group 55
(I-55)
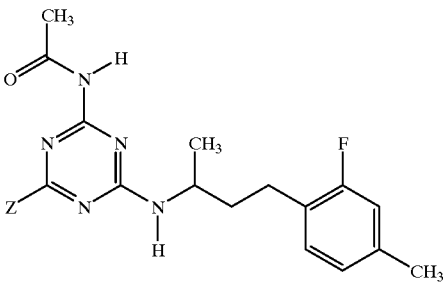
Here, Z has, for example, the meanings given above in group 1.
Group 56
(I-56)
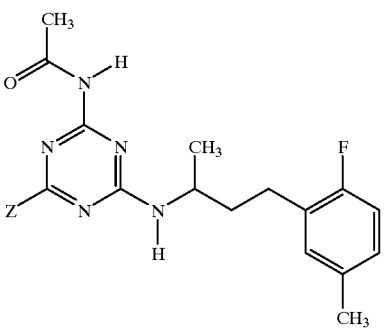
Here, Z has, for example, the meanings given above in group 1.
Group 57
(I-57)
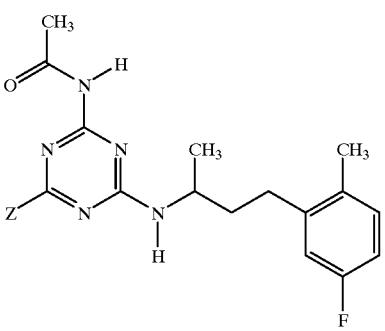

Here, Z has, for example, the meanings given above in group 1
Group 58

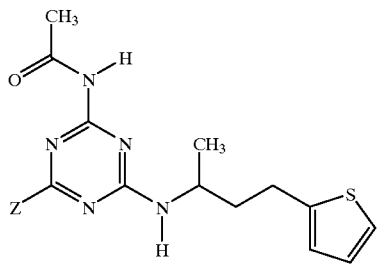
(I-58)

Here, Z has, for example, the meanings given above in group 1.
Group 59

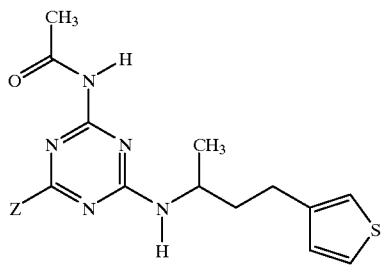
(I-59)

Here, Z has, for example, the meanings given above in group 1.
Group 60

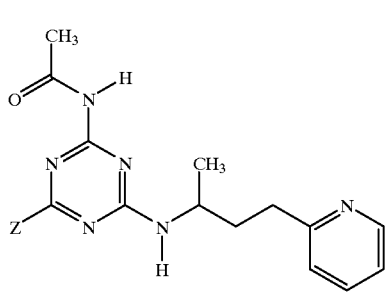
(I-60)

Here, Z has, for example, the meanings given above in group 1.

Group 61

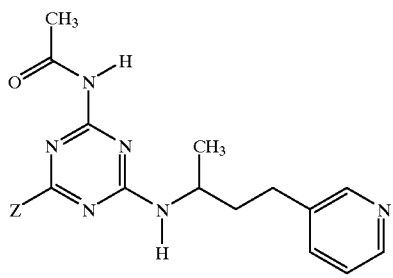
(I-61)

Here, Z has, for example, the meanings given above in group 1.
Group 62

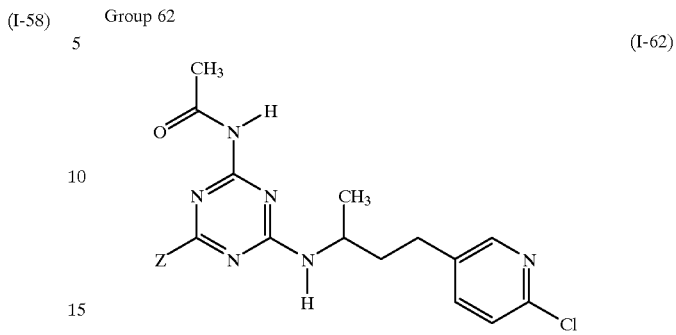
(I-62)

Here, Z has, for example, the meanings given above in group 1.
Group 63

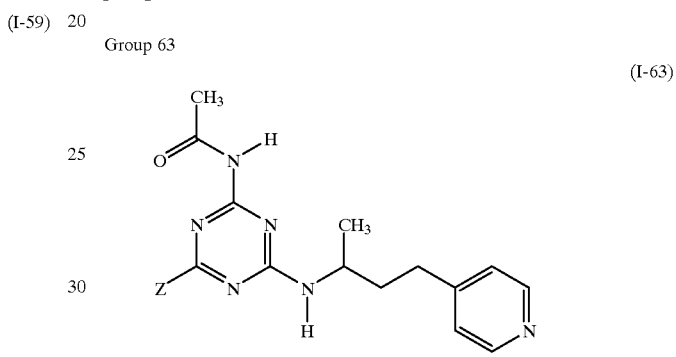
(I-63)

Here, Z has, for example, the meanings given above in group 1.

Group 64

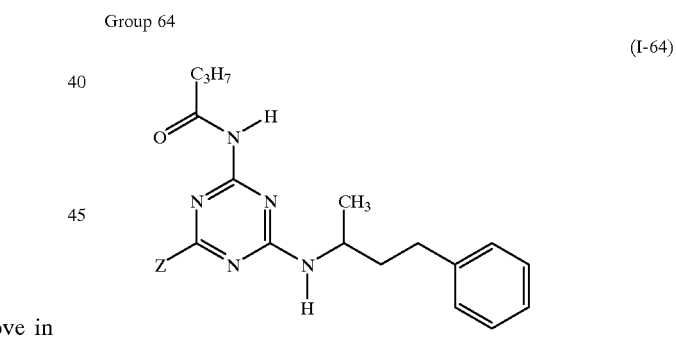
(I-64)

Here, Z has, for example, the meanings given above in group 1.

Group 65

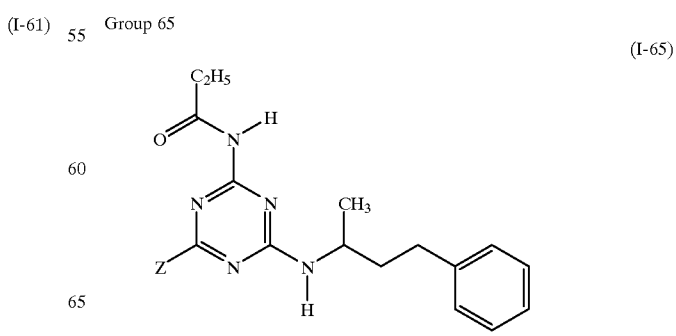
(I-65)

Group 66

(I-66)

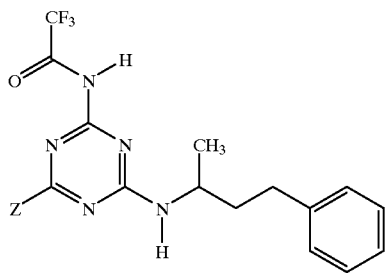

Here, Z has, for example, the meanings given above in group 1.

Group 67

(I-67)

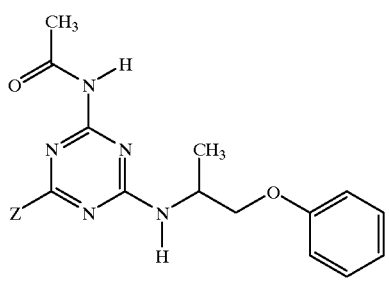

Here, Z has, for example, the meanings given above in group 1.

Group 68

(I-68)

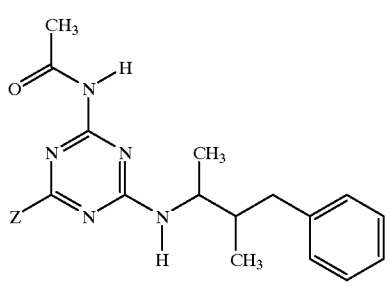

Here, Z has, for example, the meanings given above in group 1.

Group 69

(I-69)

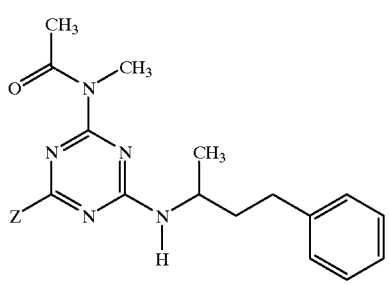

Here, Z has, for example, the meanings given above in group 1.

Group 70

(I-70)

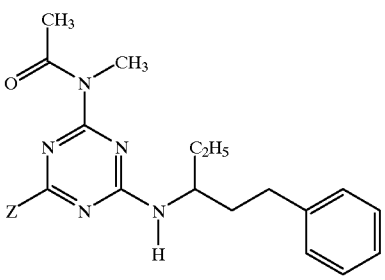

Here, Z has, for example, the meanings given above in group 1.

Group 71

(I-71)

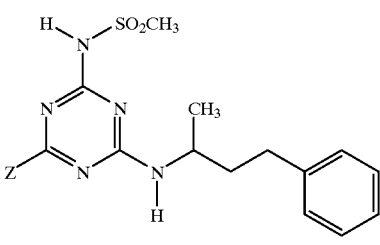

Here, Z has, for example, the meanings given above in group 1.

Group 72

(I-72)

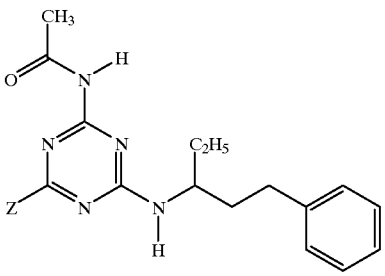

Here, Z has, for example, the meanings given above in group 1.

Group 73

(I-73)

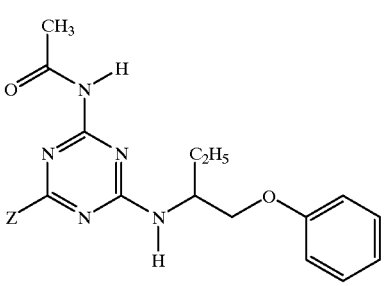

Here, Z has, for example, the meanings given above in group 1.
Group 74

(I-74)

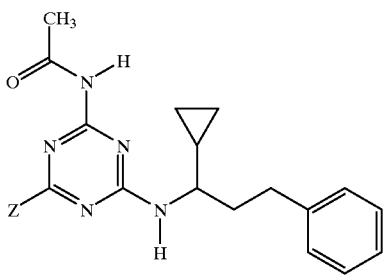

Here, Z has, for example, the meanings given above in group 1.
Group 75

(I-75)

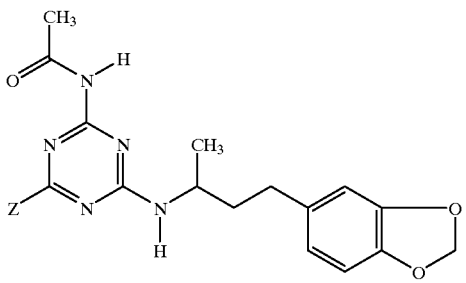

Here, Z has, for example, the meanings given above in group 1.
Group 76

(I-76)

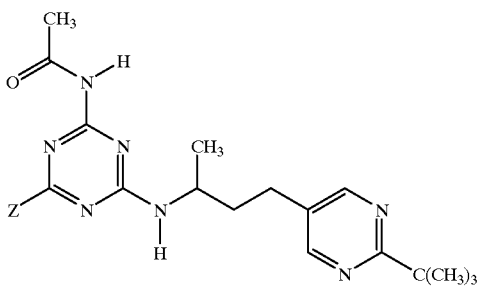

Here, Z has, for example, the meanings given above in group 1.
Group 77

(I-77)

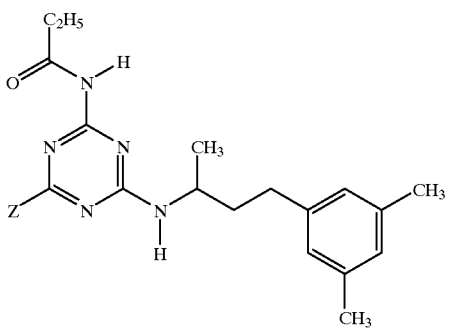

Here, Z has, for example, the meanings given above in group 1.
Group 78

(I-78)

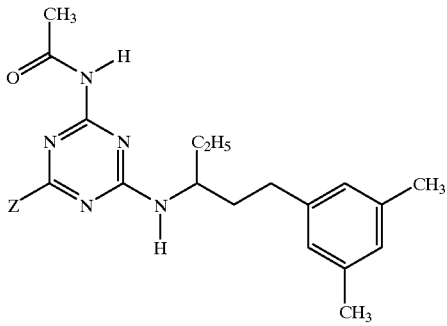

Here, Z has, for example, the meanings given above in group 1.
Group 78a (I-78a)

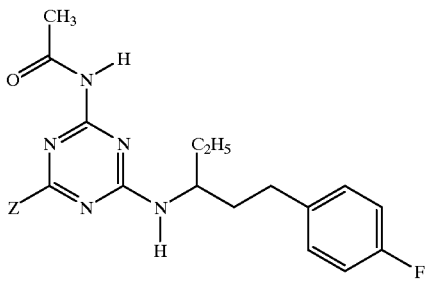

Here, Z has, for example, the meanings given above in group 1.
Group 79

(I-79)

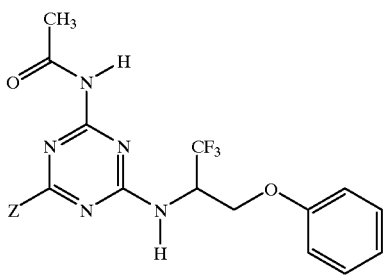

Here, Z has, for example, the meanings given above in group 1.
Group 80

(I-80)

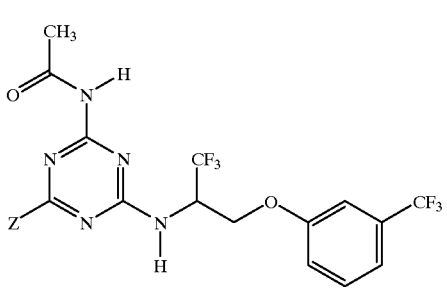

Group 81

(I-81)

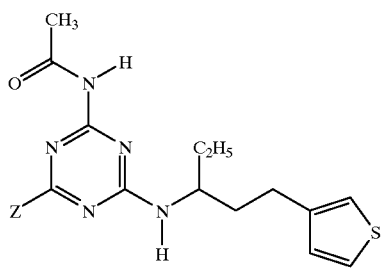

Here, Z has, for example, the meanings given above in group 1.

Group 82

(I-82)

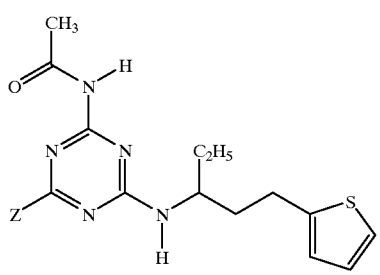

Here, Z has, for example, the meanings given above in group 1.

Group 83

(I-83)

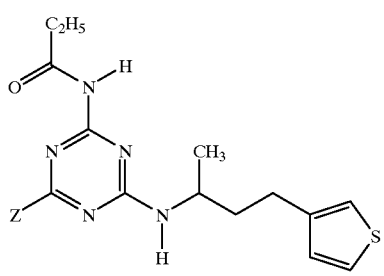

Here, Z has, for example, the meanings given above in group 1.

Group 84

(I-84)

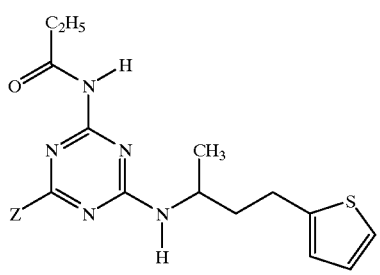

Here, Z has, for example, the meanings given above in group 1.

Group 85

(I-85)

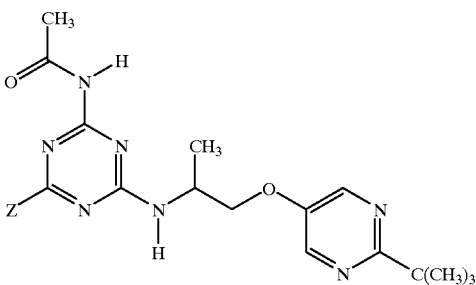

Here, Z has, for example, the meanings given above in group 1.

Group 86

(I-86)

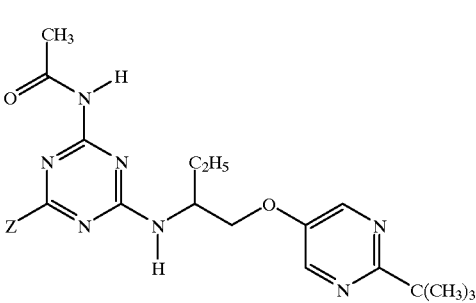

Here, Z has, for example, the meanings given above in group 1.

Group 87

(I-87)

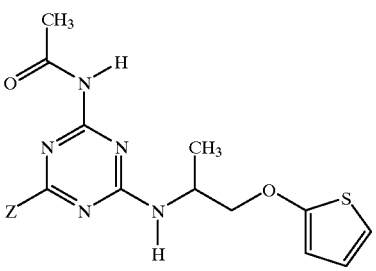

Here, Z has, for example, the meanings given above in group 1.

Group 88

(I-88)

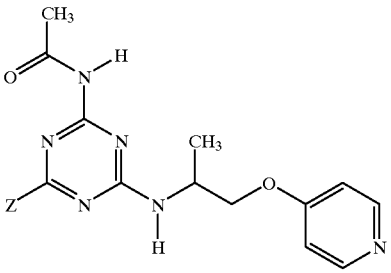

Here, Z has, for example, the meanings given above in group 1.

Group 89

(I-89)

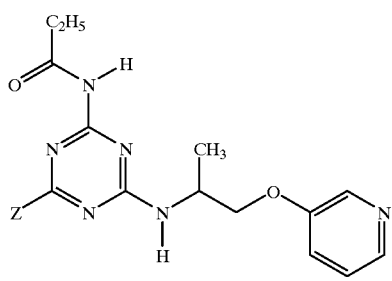

Here, Z has, for example, the meanings given above in group 1.

Group 90

(I-90)

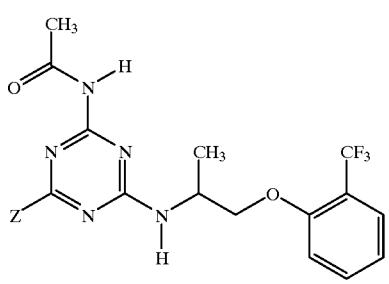

Here, Z has, for example, the meanings given above in group 1.

Group 91

(I-91)

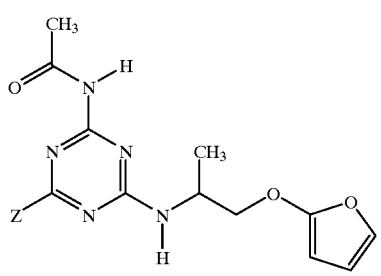

Here, Z has, for example, the meanings given above in group 1.

Group 92

(I-92)

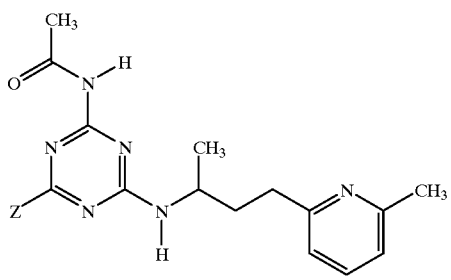

Here, Z has, for example, the meanings given above in group 1.

Group 93

(I-93)

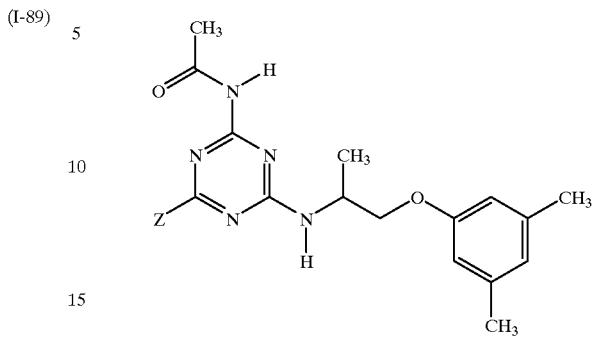

Here, Z has, for example, the meanings given above in group 1.

Group 94

(I-94)

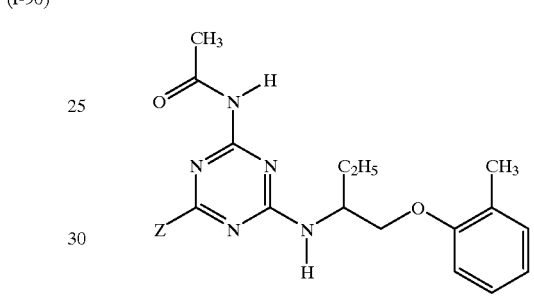

Here, Z has, for example, the meanings given above in group 1.

Group 95

(I-95)

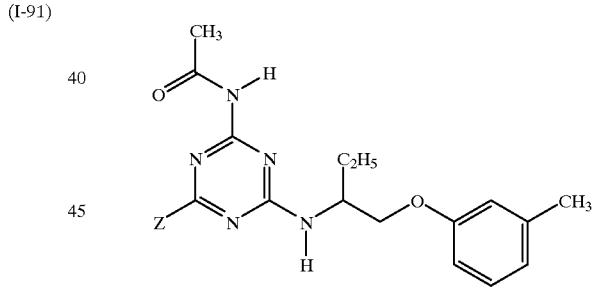

Here, Z has, for example, the meanings given above in group 1.

Group 96

(I-96)

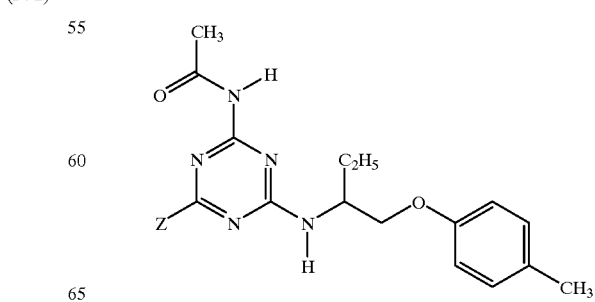

Here, Z has, for example, the meanings given above in group 1.

Group 97

(I-97)

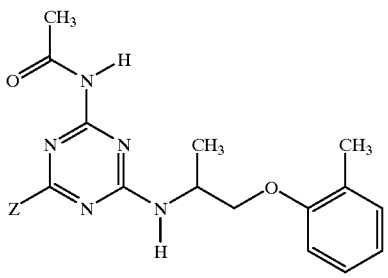

Here, Z has, for example, the meanings given above in group 1.

Group 98

(I-98)

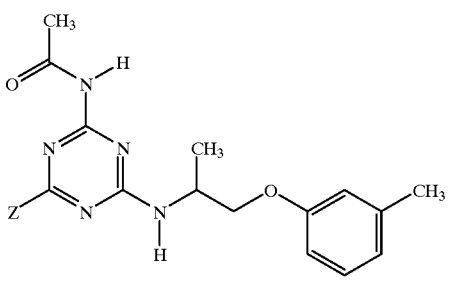

Here, Z has, for example, the meanings given above in group 1.

Group 99

(I-99)

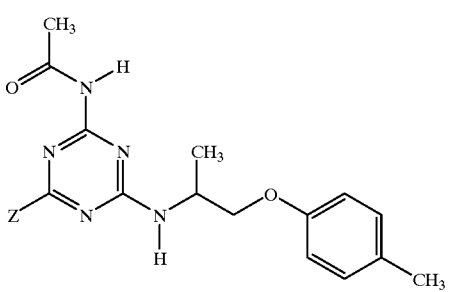

Here, Z has, for example, the meanings given above in group 1.

Group 100

(I-100)

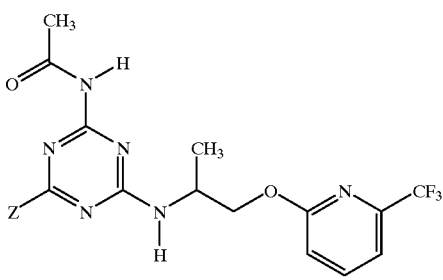

Here, Z has, for example, the meanings given above in group 1.

Group 101

(I-101)

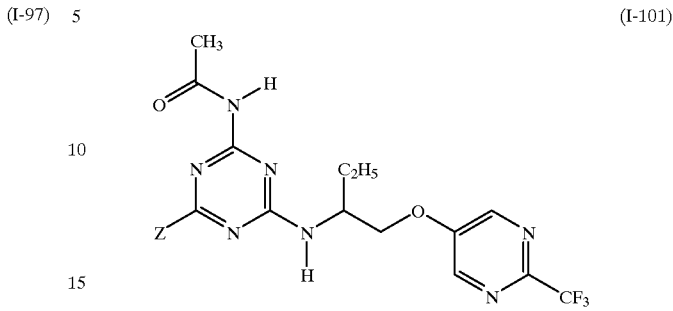

Here, Z has, for example, the meanings given above in group 1.

Group 102

(I-102)

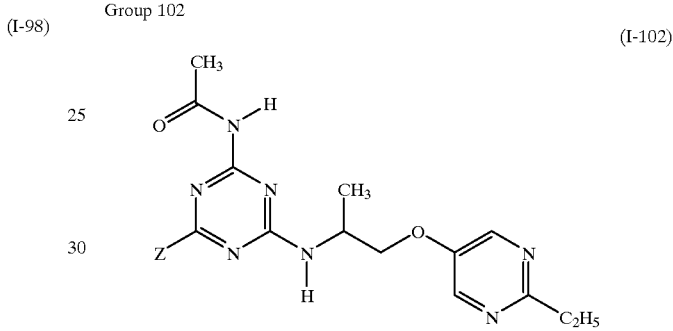

Here, Z has, for example, the meanings given above in group 1.

Using, for example, 2-methylamino-4-(1-methyl-3-phenyl-propylamino)-6-trifluoromethyl-1,3,5-triazine and propionyl chloride as starting materials, the course of the reaction in the process (a) according to the invention can be illustrated by the following equation:

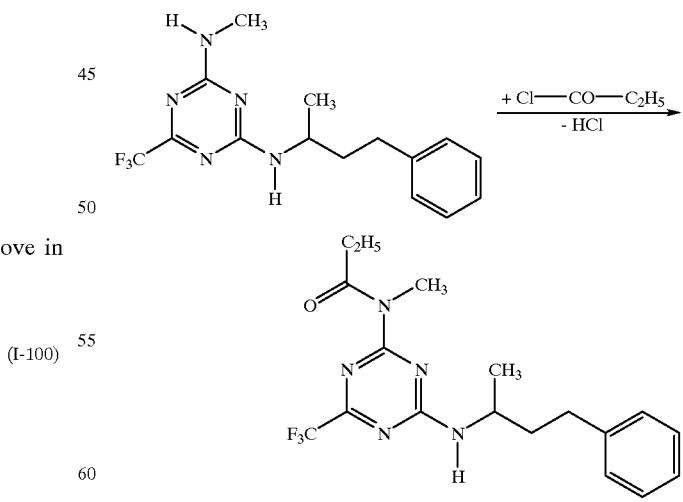

Using, for example, 1-(1-methyl-3-phenyl-propyl)-5-acetyl-5-methyl-biguanide and methyl trifluoroacetate as starting materials, the course of the reaction in the process (b) according to the invention can be illustrated by the following equation:

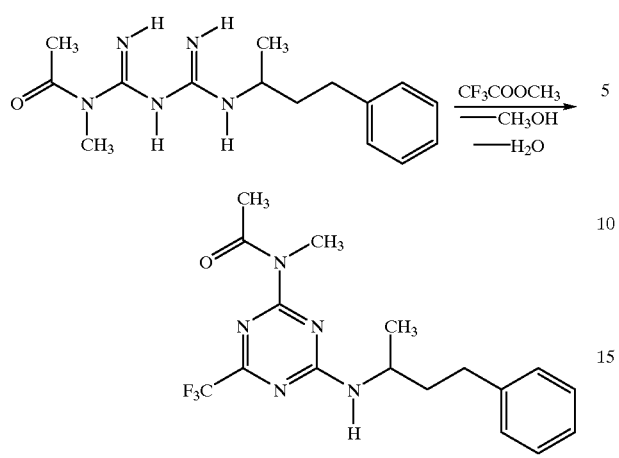

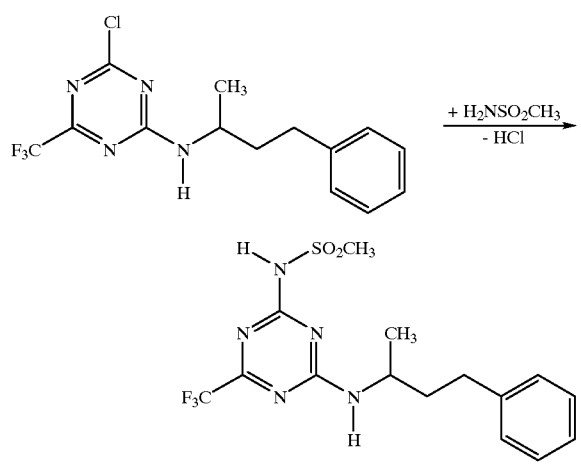

Using, for example, 2-chloro-4-(1-methyl-3-phenyl-propylamino)-6-trifluoromethyl-1,3,5-triazine and methane-sulphonamide as starting materials, the course of the reaction in the process (c) according to the invention can be illustrated by the following equation:

The formula (II) provides a general definition of the 2,4-diamino-1,3,5-triazines to be used as starting materials in the process (a) according to the invention for preparing compounds of the formula (1). In the formula (II), $R^1$, $R^3$, $R^4$, A, Ar and Z each preferably or in particular have those meanings which have already been mentioned above, in connection with the description of the compounds of the formula (I) according to the invention, as being preferred or as being particularly preferred for $R^1$, $R^3$, $R^4$, A, Ar and Z.

The starting materials of the formula (U) are known and/or can be prepared by processes known per se (cf. EP 273328, EP 411153, EP 50954, Preparation Examples); some of them also form part of the subject-matter of an application filed at the same time (cf. DE 19641693/LeA 31975).

The 2,4diamino 1,3,5-triazines of the general formula (II) are obtained when (a) substituted biguanidines of the general formula (VIII)

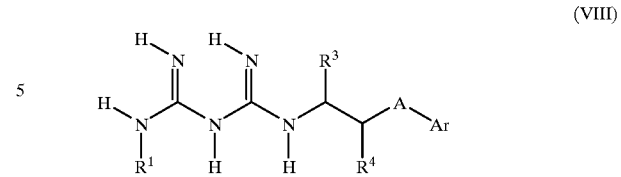

in which
$R^1$, $R^3$, $R^4$, A and Ar are each as defined above,
and/or acid adducts of compounds of the general formula (B), such as, for example, the corresponding hydrochlorides
are reacted with alkoxycarbonyl compounds of the general formula (V)

in which
Z is as defined above, with the exception of nitro, and
R' represents alkyl,
if appropriate in the presence of a reaction auxiliary, such as, for example, sodium methoxide, and if appropriate in the presence of diluent, such as, for example, methanol, at temperatures between 0° C. and 100° C.,
or when
b) substituted triazines of the general formula (IX)

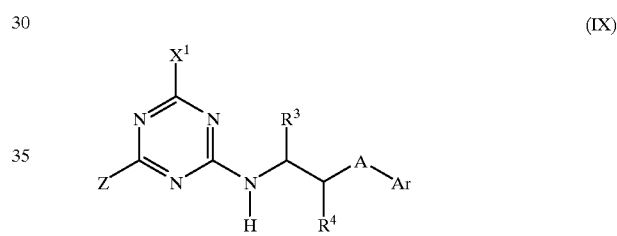

in which
$R^3$, $R^4$, A, Ar and Z are each as defined above and
$X^1$ represents halogen or alkoxy,
are reacted with amino compounds of the general formula (X)

in which
$R^1$ is as defined above,
if appropriate in the presence of a reaction auxiliary, such as, for example, potassium carbonate, and if appropriate in the presence of a diluent, such as, for example, water, methanol, ethanol or tetrahydrofuran, at temperatures between 0° C. and 100°.

The formula (III) provides a general definition of the acylating or sulphonylating agents further to be used as starting materials in the process (a) according to the invention for preparing compounds of the formula (I). In the formula (III), $R^2$ preferably or in particular has that meaning which has already been mentioned above, in connection with the description of the compounds of the formula (I) according to the invention, as being preferred or as being particularly preferred for $R^2$; Y preferably represents chlorine, bromine, iodine, methoxy, ethoxy, acetyloxy or propionyloxy.

The starting materials of the formula (Ho are known chemicals for synthesis.

The formula (IV) provides a general definition of the substituted biguanides to be used as starting materials in the process (b) according to the invention for preparing compounds of the formula (I). In the formula (IV), $R^1$, $R^2$, $R^3$, $R^4$, A and Ar each preferably or in particular have those meanings which have already been mentioned above, in connection with the description of the compounds of the formula (I) according to the invention, as being preferred or as being particularly preferred for $R^1$, $R^2$, $R^3$, $R^4$, A and Ar.

Examples of the substituted biguanides of the formula (IV) which may be mentioned are:

1-(1-methyl-3-phenyl-propyl)-, 1-(1,2-dimethyl-3-phenyl-propyl)-, 1-(1-methyl-3-(2-fluoro-phenyl)-propyl)-, 1-(1-methyl-3-(3-fluoro-phenyl)-propyl)-, 1-(1-methyl-3-(4-fluoro-phenyl)-propyl)-, 1-(1-methyl-3-(2-chloro-phenyl)-propyl)-, 1-(1-methyl-3-(3-chloro-phenyl)-propyl)-, 1-(1-methyl-3-(4chloro-phenyl)-propyl)-, 1-(1-methyl-3-(2-bromo-phenyl)-propyl)-, 1-(1-methyl-3-(3-bromo-phenyl)-propyl)-, 1-(1-methyl-3-(4-bromo-phenyl)-propyl)-, 1-(1-methyl-3-(2-nitro-phenyl)-propyl)-, 1-(1-methyl-3-(3-nitro-phenyl)-propyl)-, 1-(1-methyl-3-(4-nitro-phenyl)-propyl)-, 1-(1-methyl-3-(2-methyl-phenyl)-propyl)-, 1-(1-methyl-3-(3-methyl-phenyl)-propyl)-, 1-(1-methyl-3-(4-methyl-phenyl)-propyl)-, 1-(1-methyl-3-(2-trifluoromethyl-phenyl)-propyl)-, 1-(1-methyl-3-(3-trifluoromethyl-phenyl)-propyl)-, 1-(I -methyl-3-(4-trifluoromethyl-phenyl)-propyl)-, 1-(1-methyl-3-(2-methoxy-phenyl)-propyl)-, 1-(1-methyl-3-(3-methoxy-phenyl)-propyl)-, 1-(1-methyl-3-(4-methoxy-phenyl)-propyl)-, 1-(1-methyl-3-(2-difluoromethoxy-phenyl)-propyl)-, 1-(1-methyl-3-(2-difluoromethoxy-phenyl)-propyl)-, 1-(1-methyl-3-(2-difluoromethoxy-phenyl)-propyl)-, 1-(1-methyl-3-(2-trifluoromethoxy-phenyl)-propyl)-, 1-(1-methyl-3-(3-trifluoromethoxy-phenyl)-propyl), 1-(1-methyl-3-(4-trifluoromethoxy-phenyl)-propyl)-, 1-(1-methyl-3-(2-methoxycarbonyl-phenyl)-propyl)-, carbonyl-phenyl)-propyl)-, 1-(1-methyl-3-(2-ethoxycarbonyl-phenyl)-propyl)-, 1-(1-methyl-3-(4-methoxycarbonyl-phenyl)-propyl)-, 1-(1-methyl-3-(4-ethoxycarbonyl-phenyl)-propyl)-, 1-(1-methyl-3-(2-methylthiophenyl)-propyl)-, 1-(1-methyl-3-(4-methylthio-phenyl)-propyl)-, 1-(1-methyl-3-(2-methylsulphinyl-phenyl)-propyl)-, 1-(1-methyl-3-(4-methylsulphinyl-phenyl)-propyl)-, 1-(1-methyl-3-(2-methylsulphonyl-phenyl)-propyl)-, 1-(1-methyl-3-(4-methylsulphonyl-phenyl)-propyl)-, 1-(1-methyl-3-(3,4-dichloro-phenyl)-propyl)-, 1-(1-methyl-3-(2,4-dichloro-phenyl)-propyl)-, 1-(1-methyl-3-(2,5-dichloro-phenyl)-propyl)-, 1-(1-methyl-3-(2,6-dichloro-phenyl)-propyl)-, 1-(1-methyl-3-(2,6-difluoro-phenyl)-propyl)-, 1-(1-methyl-3-(2,5-difluoro-phenyl)-propyl)-, 1-(1-methyl-3-(2,4-difluoro-phenyl)-propyl)-, 1-(I-methyl-3-(3,4-difluoro-phenyl)-propyl)-, 1-(1-methyl-3-(3,5-difluoro-phenyl)-propyl)-, 1-(1-methyl-3-(2-fluoro-4-chloro-phenyl)-propyl)-, 1-(1-methyl-3-(4-fluoro-2-chlorophenyl)-propyl)-, 1-(1-methyl-3-(2,4-dimethyl-phenyl)-propyl)-, 1-(1-methyl-3-(3,4-dimethyl-phenyl)-propyl)-, 1-(1-methyl-3-(3,5-dimethyl-phenyl)-propyl)-, 1-(I-methyl-3-(2,5-dimethyl-phenyl)propyl)-, 1-(1-methyl-3-(2-chloro-6-methyl-phenyl)-propyl)-, 1-(1-methyl-3-(4-fluoro-2-methyl-phenyl)-propyl)-, 1-(1-methyl-3-(2-fluoro-4-methyl-phenyl)-propyl)-, 1-(1-methyl-3-(2-fluoro-5-methyl-phenyl)-propyl)-, 1-(1-methyl-3-(5-fluoro-2-methyl-phenyl)-propyl)-, 1-(1-methyl-3-thien-2-yl-propyl)-, 1-(1-methyl-3-thien-3-yl-propyl)-, 1-(1-methyl-3-pyridin-2-yl-propyl)-, 1-(1-methyl-3-pyridin-3-yl-propyl)- and 1-(1-methyl-3-pyridin-4-yl-propyl)-5-acetyl-5-methyl-biguanide-5-acetyl-5-ethyl-biguanide, -5-methyl-5-propionyl-biguanide, -5-acetyl-biguanide, -5-propionyl-biguanide, 5-trifluoroacetyl-biguanide, 5-methylsulphonyl-biguanide and -5-ethylsulphonyl-biguanide.

The starting materials of the general formula (IV) have hitherto not been disclosed in the literature; as novel substances, they also form part of the subject-matter of the present application.

The novel substituted biguanidines of the general formula (IV) are obtained when substituted alkylamino compounds of the general formula (XI)

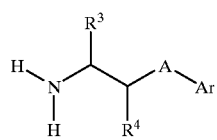

(XI)

in which
$R^3$, $R^4$, A and Ar are each as defined above,
and/or acid adducts of compounds of the general formula (XI), such as, for example, the hydrochlorides
are reacted with substituted cyanoguanidines of the general formula (XII)

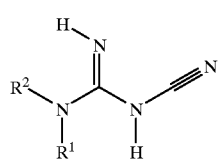

(XII)

in which
$R^1$ and $R^2$ are each as defined above,
if appropriate in the presence of a reaction auxiliary, such as, for example, hydrogen chloride, and if appropriate in the presence of a diluent, such as, for example, n-decane or 1,2-dichloro-benzene, at temperatures between 100° C. and 200° C. (cf EP 492615, Preparation Examples).

The substituted alkylamino compounds of the general formula (XI) required as intermediates for this purpose are known and/or can be prepared by processes known per se (cf. DE 3426919; DE 4000610; DE 4332738, EP 320898; EP 443606:) Tetrahedron: Asymmetry 5 (1994), 817-820; Tetrahedron Lett. 29 (1988), 223–224; loc. cit. 36 (1995), 3917–3920; Preparation Examples).

The formula (V) provides a general definition of the alkoxycarbonyl compounds further to be used as starting materials in the process (b) according to the invention for preparing compounds of the formula (I). In the formula (V), Z preferably or in particular has that meaning which has already been mentioned above, in connection with the description of the compounds of the formula (I) according to the invention, as being preferred or as being particularly preferred for Z; $R^1$ preferably represents alkyl having 1 to 4 carbon atoms, and in particular represents methyl or ethyl.

The starting materials of the formula (V) are known chemicals for synthesis.

The formula (VI) provides a general definition of the substituted halogenotriazines to be used as starting materials in the process (c) according to the invention for preparing compounds of the formula (I). In the formula (VI), $R^3$, $R^4$, A, Ar and Z each preferably or in particular have those meanings which have already been mentioned above, in connection with the description of the compounds of the formula (I) according to the invention, as being preferred or as being particularly preferred for R³, R⁴, A, Ar and Z; X preferably represents fluorine, chlorine or bromine, and in particular represents chlorine.

The starting materials of the general formula (VI) have hitherto not been disclosed in the literature; as novel substances, they also form part of the subject-matter of an application which was filed at the same time (cf. DE 196 41 693.0).

The novel substituted halogenotriazines of the general formula (VI) are obtained when triazines of the general formula (XIII)

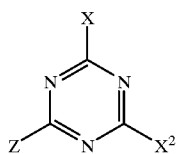

(XIII)

in which
X and Z are each as defined above and
X² represents halogen
are reacted with substituted alkylamino compounds of the general formula (XI)

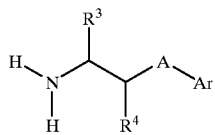

(XI)

in which
R³, R⁴, A and Ar are each as defined above,
if appropriate in the presence of an acid acceptor, such as, for example, ethyldiisopropylamine, and if appropriate in the presence of a diluent, such as, for example, tetrahydrofuran or dioxane, at temperatures between −50° C. and +50° C. (cf. the Preparation Examples).

The formula (VII) provides a general definition of the nitrogen compounds further to be used as starting materials in the process (c) according to the invention for preparing compounds of the formula (I). In the formula (VII), R¹ and R² preferably or in particular have those meanings which have already been mentioned above, in connection with the description of the compounds of the formula (I) according to the invention, as being preferred or as being particularly preferred for R¹ and R².

The starting materials of the formula (VII) are known chemicals for synthesis.

If appropriate, the processes according to the invention for preparing the compounds of the formula (I) are carried out using a reaction auxiliary. Suitable reaction auxiliaries for the processes (a), (b) and (c) are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylmine, N,N-dimethyl-cyclohexylamine, dicyclohexylamine, ethyl-dicyclohexylamine, N,N-dimethylaniline, N,N-dimethyl-benzylamine, pyridine, 2-methyl-, 3-methyl-, 4-ethyl-2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo-[2,2,2]-octane (DABCO), 1,5-diazabicyclo[4,3,0]-non-5-ene (DBN), or 1,8-diaza-bicyclo [5,4,0]-undec-7-ene (DBU).

Suitable diluents for carrying out the processes (a), (b) and (c) according to the invention are especially inert organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl or diethyl ether, ketones, such as methyl isopropyl ketone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate; sulphoxides, such as dimethyl sulphoxide; alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

In the practice of the processes (a), (b) and (c) according to the invention, the reaction temperatures can be varied over a relatively wide range. Generally, the reaction is carried out at temperatures between 0° C. and 200° C., preferably between 10° C. and 150° C.

The processes (a), (b))and (c) according to the invention are generally carried out at atmospheric pressure. However, it is also possible to carry out the processes according to the invention under elevated or reduced pressure—generally between 0.1 bar and 10 bar.

In the practice of the processes according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stiffed for several hours at the temperature required. Work-up is carried out by conventional methods (cf. the Preparation Examples).

The active compounds according to the invention can be used as defoliants, desiccants, haulm killers and, especially, as weed-killers. By weeds in the broadest sense, there are to be understood all plants which grow in locations where they are undesirable. Whether the substances according to the invention act as total or selective herbicides depends essentially on the amount used.

The active compounds according to the invention can be used, for example, in connection with the following plants: Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera and Phalaris.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture land, and for the selective control of weeds in annual cultures.

The compounds of the formula (I) according to the invention are suitable in particular for selectively controlling monocotyledonous and dicotyledonous weeds in monocotyledonous and dikotyledonous crops, both preemergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example
acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfuron(-methyl), ethofumesate, ethoxyfen, etobenzanid, fenoxaprop-ethyl, flamprop(-isopropyl), flamprop(-isopropyl-L), flamprop(-methyl), flazasulfuron, fluazifop(-butyl), flumetsulam, flumiclorac (-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-ammonium), glyphosate(-isopropylammonium), halosafen, haloxyfop (-ethoxyethyl), hexazinone, imazamethabenz(-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron(-methyl), molinate, monolinuron, naproanilide, napropamide, neburon, nicosulfuron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium) quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluaride, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha The preparation and use of the active compounds according to the invention can be seen from the Examples below.

PREPARATION EXAMPLES

Example 1

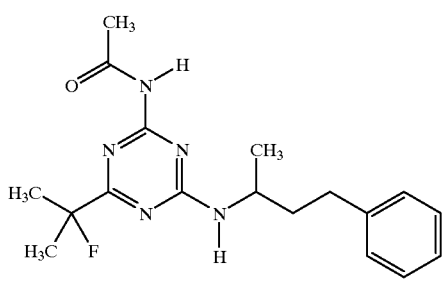

(Process (a))

A mixture of 1.86 g (6.14 mmol) of 2-amino-4-(1-methyl-3-phenyl-propylamino)-6-(1-fluoro-1-methyl-ethyl)-1,3,5-triazine (racemic), 0.33 g (6.14 mmol) of sodium methoxide and 6 ml methanol is heated to approximately 50° C. for one hour and then concentrated under water pump vacuum. The residue is, after addition of 12 ml of ethyl acetate, heated at about 50° C. for one hour and, after cooling, shaken with 20 ml of water. The organic phase is dried with sodium sulphate and filtered. The filtrate is concentrated under water pump vacuum and the residue is purified by column chromatography.

This gives 0.96 g of 2-acetylamino-4-(1-methyl-3-phenyl-propylamino)-6-(1-fluoro 1-methyl-ethyl)-1,3,5-triazine (racemate) as colourless crystals of melting point 91° C.

Example 2

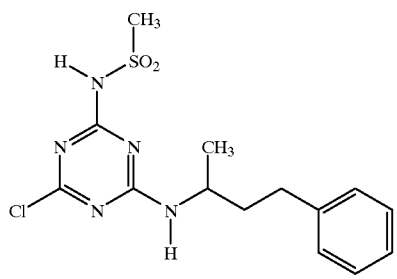

(Process (c))

A mixture of 3.0 g (10.1 mmol) of 2,4-dichloro-6-(1-methyl-3-phenyl-propyl-amino)-1,3,5-triazine (racemic), 3.3 g (25 mmol) of potassium carbonate, 1.2 g (12.2 mmol) of methanesulphonamide and 15 ml N-methyl-pyrrolidone is stirred at 100° C. for three hours. After cooling, the mixture is shaken with ethyl acetate/aqueous phosphoric acid, and the organic phase is separated off, dried with sodium sulphate and filtered. The filtrate is concentrated under water pump vacuum and the residue is purified by column chromatography (silica gel, ethyl acetate/hexane, ratio by volume 1:1).

This gives 2.2 g (61% of theory) of 2-chloro-4-methylsulphonylamino-6-(1-methyl-3-phenyl-propylamino)-1,3,5-triazine (racemate) as white crystals of melting point 143° C.

By the methods of Preparation Examples 1 and 2, and in accordance with the general description of the preparation processes according to the invention, it is also possible to prepare, for example, the compounds of the formula (I) listed in Table 1 below.

(I)

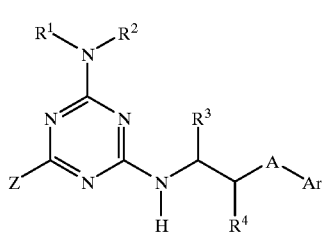

TABLE 1

Examples of compounds of the formula (I)

| Ex. No. | $R^1$ | $R^2$ | $R^3$ | $R^4$ | A | Ar | Z | Physical data and stereochemical specifications |
|---|---|---|---|---|---|---|---|---|
| 3 | H | $SO_2CH_3$ | $CH_3$ | H | $CH_2$ | phenyl | $OCH_3$ | m.p.: 125° C. (racemate) |
| 4 | H | $SO_2CH_3$ | $CH_3$ | H | $CH_2$ | phenyl | $OCH_2CF_3$ | (amorphous) (racemate) |
| 5 | H | $SO_2CH_3$ | $CH_3$ | H | $CH_2$ | phenyl | $SCH_3$ | (amorphous) (racemate) |
| 6 | H | $COCH_3$ | $CH_3$ | H | $CH_2$ | phenyl | $SCH_3$ | m.p.: 131° C. (racemate) |
| 7 | H | $COCH_3$ | $CH_3$ | H | O | phenyl | $CF_3$ | m.p.: 145° C. (racemate) |
| 8 | H | $COCH_3$ | $CH_3$ | H | O | phenyl | $CF_3$ | m.p.: 112° C. (R enantiomer) |
| 9 | H | $COCH_3$ | $CH_3$ | H | O | phenyl | $CF_3$ | m.p.: 111° C. (S enantiomer) |
| 10 | H | $COCH_3$ | $CH_3$ | H | $CH_2$ | 4-$OCH_3$-phenyl | $CF_3$ | m.p.: 115° C. (racemate) |
| 11 | H | $COCH_3$ | $CH_3$ | H | $CH_2$ | 4-$OCH_3$-phenyl | $CF_3$ | m.p.: 113° C. (R enantiomer) |
| 12 | H | $COCH_3$ | $CH_3$ | H | $CH_2$ | 4-$OCH_3$-phenyl | $CF_3$ | (amorphous) (S enantiomer) |
| 13 | H | $COCH_3$ | $CH_3$ | H | $CH_2$ | phenyl | $CHFCH_3$ | (racemate) |
| 14 | H | $COCH_3$ | $CH_3$ | H | $CH_2$ | phenyl | $CHFCH_3$ | (R enantiomer) |

TABLE 1-continued

Examples of compounds of the formula (I)

| Ex. No. | R$^1$ | R$^2$ | R$^3$ | R$^4$ | A | Ar | Z | Physical data and stereochemical specifications |
|---|---|---|---|---|---|---|---|---|
| 15 | H | COCH$_3$ | CH$_3$ | H | CH$_2$ | phenyl | CHFCH$_3$ | (S enantiomer) |
| 16 | H | COCH$_3$ | CH$_3$ | H | CH$_2$ | phenyl | CF(CH$_3$)$_2$ | (racemate) |
| 17 | H | COCH$_3$ | CH$_3$ | H | CH$_2$ | phenyl | CF(CH$_3$)$_2$ | (R enantiomer) |
| 18 | H | COCH$_3$ | CH$_3$ | H | CH$_2$ | phenyl | CF(CH$_3$)$_2$ | (S enantiomer) |
| 19 | H | COCH$_3$ | CH$_3$ | H | CH$_2$ | phenyl | C$_2$F$_5$ | (racemate) |
| 20 | H | COCH$_3$ | CH$_3$ | H | CH$_2$ | phenyl | CHFCF$_3$ | (racemate) |
| 21 | H | COCH$_3$ | CH$_3$ | H | CH$_2$ | phenyl | CHCl$_2$ | (racemate) |
| 22 | H | COCH$_3$ | CH$_3$ | H | CH$_2$ | phenyl | CH$_2$Cl | (racemate) |
| 23 | H | COCH$_3$ | CH$_3$ | H | CH$_2$ | phenyl | CHClCH$_3$ | (racemate) |
| 24 | H | COCH$_3$ | CH$_3$ | H | CH$_2$ | phenyl | CCl$_2$CH$_3$ | (racemate) |
| 25 | H | COCH$_3$ | CH$_3$ | H | CH$_2$ | 3,5-dimethylphenyl | CF(CH$_3$)$_2$ | (racemate) |

TABLE 1-continued

Examples of compounds of the formula (I)

| Ex. No. | R¹ | R² | R³ | R⁴ | A | Ar | Z | Physical data and stereochemical specifications |
|---|---|---|---|---|---|---|---|---|
| 26 | H | COCH₃ | CH₃ | H | CH₂ | 4-SCH₃-C₆H₄ | CF(CH₃)₂ | m.p.: 88° C. (racemate) |
| 27 | H | COCH₃ | C₂H₅ | H | CH₂ | C₆H₅ | CF₃ | m.p.: 143° C. (racemate) |
| 28 | H | COCH₃ | C₂H₅ | H | CH₂ | C₆H₅ | CF₃ | (amorphous) (R enantiomer) |
| 29 | H | COCH₃ | C₂H₅ | H | CH₂ | C₆H₅ | CF₃ | m.p.: 78° C. (S enantiomer) |
| 30 | H | COCH₃ | C₂H₅ | H | O | C₆H₅ | CF₃ | m.p.: 136° C. (racemate) |
| 31 | H | COCH₃ | C₂H₅ | H | O | C₆H₅ | CF₃ | m.p.: 99° C. (R enantiomer) |
| 32 | H | COCH₃ | C₂H₅ | H | O | C₆H₅ | CF₃ | mp: 102° C. (S enantiomer) |
| 33 | H | COCH₃ | C₂H₅ | H | CH₂ | 4-SCH₃-C₆H₄ | CF(CH₃)₂ | $n_D^{20}$ = 1.5735 (racemate) |
| 34 | H | COCH₃ | C₂H₅ | H | CH₂ | 4-OCH₃-C₆H₄ | CF(CH₃)₂ | (racemate) |
| 35 | H | COCH₃ | C₂H₅ | H | CH₂ | 4-Cl-C₆H₄ | CF(CH₃)₂ | (racemate) |
| 36 | H | COCH₃ | CH₃ | H | CH₂ | 4-CH₃-C₆H₄ | CF(CH₃)₂ | (racemate) |

TABLE 1-continued

Examples of compounds of the formula (I)

| Ex. No. | R¹ | R² | R³ | R⁴ | A | Ar | Z | Physical data and stereochemical specifications |
|---|---|---|---|---|---|---|---|---|
| 37 | H | COCH₃ | CH₃ | H | CH₂ | 4-(SCH₃)C₆H₄ | CF₃ | m.p.: 116° (racemate) |
| 38 | H | COCH₃ | CH₃ | H | CH₂ | 4-(SOCH₃)C₆H₄ | CF₃ | (amorphous) (racemate) |
| 39 | H | COCH₃ | CH₃ | H | CH₂ | 4-(SO₂CH₃)C₆H₄ | CF₃ | m.p.: 144° C. (racemate) |
| 40 | H | COCH₃ | CH₃ | H | CH₂ | 4-(SOCH₃)C₆H₄ | CF(CH₃)₂ | (amorphous) (racemate) |
| 41 | H | COCH₃ | CH₃ | H | CH₂ | 4-(SO₂CH₃)C₆H₄ | CF(CH₃)₂ | m.p.: 147° C. (racemate) |
| 42 | H | COCH₃ | CH₃ | H | CH₂ | 4-(SCH₃)C₆H₄ | CH(OCH₃)CH₃ | m.p.: 109° C. (racemate) |
| 43 | H | COCH₃ | CH₃ | H | CH₂ | 4-(SO₂CH₃)C₆H₄ | CH(OCH₃)CH₃ | m.p.: 135° C. (racemate) |
| 44 | H | COCH₃ | CH₃ | H | CH₂ | 4-(SCH₃)C₆H₄ | CHFCH₃ | m.p.: 96° C. (racemate) |
| 45 | H | COCH₃ | CH₃ | H | CH₂ | 4-(SOCH₃)C₆H₄ | CHFCH₃ | (amorphous) (racemate) |
| 46 | H | COCH₃ | CH₃ | H | CH₂ | 4-(SO₂CH₃)C₆H₄ | CHFCH₃ | m.p.: 139° C. (racemate) |
| 47 | H | COCH₃ | C₃H₇-i | H | CH₂ | 4-Cl-C₆H₄ | CF₃ | m.p.: 134° C. (racemate) |

TABLE 1-continued

Examples of compounds of the formula (I)

| Ex. No. | R¹ | R² | R³ | R⁴ | A | Ar | Z | Physical data and stereochemical specifications |
|---|---|---|---|---|---|---|---|---|
| 48 | H | COCH₃ | C₃H₇-i | H | CH₂ | 4-Cl-C₆H₄ | CHFCH₃ | m.p.: 123° C. (racemate) |
| 49 | H | COCH₃ | C₃H₇-i | H | CH₂ | 4-Cl-C₆H₄ | CF(CH₃)₂ | m.p.: 126° C. (racemate) |
| 50 | H | COCH₃ | C₃H₇-n | H | CH₂ | 4-Cl-C₆H₄ | CF(CH₃)₂ | m.p.: 94° C. (racemate) |
| 51 | H | COCH₃ | C₃H₇-n | H | CH₂ | 4-Cl-C₆H₄ | CHFCH₃ | m.p.: 96° C. (racemate) |
| 52 | H | COCH₃ | C₃H₇-n | H | CH₂ | 4-Cl-C₆H₄ | CF₃ | m.p.: 114° C. (racemate) |
| 53 | H | COCH₃ | CH₃ | H | O | 3,5-(CH₃)₂-C₆H₃ | C₂H₅ | m.p.: 143° C. (racemate) |
| 54 | H | COCH₃ | CH₃ | H | O | 3,5-(CH₃)₂-C₆H₃ | CHCl₂ | m.p.: 153° C. (racemate) |
| 55 | H | COCH₃ | CH₃ | H | O | 3,5-(CH₃)₂-C₆H₃ | CH₂Cl | m.p.: 130° C. (racemate) |
| 56 | H | COCH₃ | CH₃ | H | O | 3,5-(CH₃)₂-C₆H₃ | CHFCF₃ | m.p.: 100° C. (racemate) |
| 57 | H | COCH₃ | CH₃ | H | O | 3,5-(CH₃)₂-C₆H₃ | CHClCH₃ | m.p.: 135° C. (racemate) |

TABLE 1-continued

Examples of compounds of the formula (I)

| Ex. No. | R¹ | R² | R³ | R⁴ | A | Ar | Z | Physical data and stereochemical specifications |
|---|---|---|---|---|---|---|---|---|
| 58 | H | COCH$_3$ | C$_2$H$_5$ | H | O | 5-methyl-2-(C(CH$_3$)$_3$)-pyrimidinyl | CF$_3$ | $n_D^{20}$ = 1.5007 (racemate) |
| 59 | H | COCH$_3$ | C$_2$H$_5$ | H | O | 5-methyl-2-(C(CH$_3$)$_3$)-pyrimidinyl | CHFCH$_3$ | (amorphous) (racemate) |
| 60 | H | COCH$_3$ | C$_2$H$_5$ | H | O | 5-methyl-2-(C(CH$_3$)$_3$)-pyrimidinyl | CF(CH$_3$)$_2$ | (amorphous) (racemate) |
| 61 | H | COCH$_3$ | C$_2$H$_5$ | H | O | 5-methyl-2-(C(CH$_3$)$_3$)-pyrimidinyl | C$_2$H$_5$ | (amorphous) (racemate) |
| 62 | H | COCH$_3$ | C$_2$H$_5$ | H | O | phenyl | CHFCH$_3$ | m.p.: 126° C. (racemate) |
| 63 | H | COCH$_3$ | C$_2$H$_5$ | H | O | phenyl | C$_2$H$_5$ | m.p.: 98° C. (racemate) |
| 64 | H | COCH$_3$ | CH$_3$ | H | CH$_2$ | phenyl | CF$_3$ | m.p.: 141° C. (racemate) |
| 65 | H | COCH$_3$ | C$_2$H$_5$ | H | O | 4-chlorophenyl | CF$_3$ | m.p.: 150° C. (racemate) |
| 66 | H | COCH$_3$ | CH$_3$ | H | CH$_2$ | phenyl | CF$_3$ | m.p.: 139° C. (R enantiomer) |
| 67 | H | COCH$_3$ | CH$_3$ | H | CH$_2$ | phenyl | CF$_3$ | m.p.: 100° C. (S enantiomer) |
| 68 | H | COCH$_3$ | C$_2$H$_5$ | H | O | 4-chlorophenyl | CF$_3$ | m.p.: 99° C. (R enantiomer) |

TABLE 1-continued

Examples of compounds of the formula (I)

| Ex. No. | R¹ | R² | R³ | R⁴ | A | Ar | Z | Physical data and stereochemical specifications |
|---|---|---|---|---|---|---|---|---|
| 69 | H | COCH$_3$ | C$_2$H$_5$ | H | O | 4-Cl-C$_6$H$_4$ | CF$_3$ | m.p.: 106° C. (S enantiomer) |
| 70 | H | COC$_2$H$_5$ | CH$_3$ | H | CH$_2$ | C$_6$H$_5$ | CF(CH$_3$)$_2$ | (amorphous) (racemate) |
| 71 | H | COOCH$_3$ | CH$_3$ | H | CH$_2$ | C$_6$H$_5$ | CF(CH$_3$)$_2$ | (amorphous) (racemate) |
| 72 | H | COCH$_3$ | C$_2$H$_5$ | H | CH$_2$ | 4-SCH$_3$-C$_6$H$_4$ | CF$_3$ | (amorphous) (racemate) |
| 73 | H | COCH$_3$ | C$_2$H$_5$ | H | CH$_2$ | 4-SCH$_3$-C$_6$H$_4$ | CHFCH$_3$ | (amorphous) (racemate) |
| 74 | H | COCH$_3$ | CH$_3$ | H | O | 3,5-(CH$_3$)$_2$-C$_6$H$_3$ | CH=CH$_2$ | m.p.: 107° C. (racemate) |
| 75 | H | COCH$_3$ | CH$_3$ | H | CH$_2$ | 3-methylthiophene | CH=CH-OCH$_3$ | m.p.: 141° C. (racemate) |
| 76 | H | COCH$_3$ | CH$_3$ | H | CH$_2$ | 2-methylthiophene | CH=CH-OCH$_3$ | m.p.: 142° C. (racemate) |
| 77 | H | COCH$_3$ | CH$_3$ | H | O | C$_6$H$_5$ | CH$_2$CH$_2$-OCH$_3$ | (amorphous) (racemate) |
| 78 | H | COCH(CH$_3$)$_2$ | CH$_3$ | H | CH$_2$ | C$_6$H$_5$ | CF(CH$_3$)$_2$ | (amorphous) (racemate) |
| 79 | H | COC(CH$_3$)$_3$ | CH$_3$ | H | CH$_2$ | C$_6$H$_5$ | CF(CH$_3$)$_2$ | (amorphous) (racemate) |

TABLE 1-continued

Examples of compounds of the formula (I)

| Ex. No. | R¹ | R² | R³ | R⁴ | A | Ar | Z | Physical data and stereochemical specifications |
|---|---|---|---|---|---|---|---|---|
| 80 | H | $COC_2H_5$ | $CH_3$ | H | $CH_2$ | 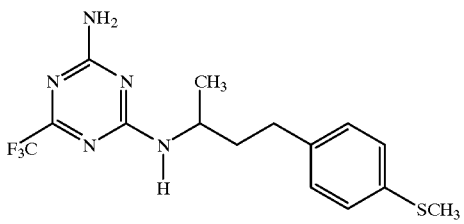 | $CF(CH_3)_2$ | (amorphous) (racemate) |

Starting Materials of the Formula (II):

Example (II-1)

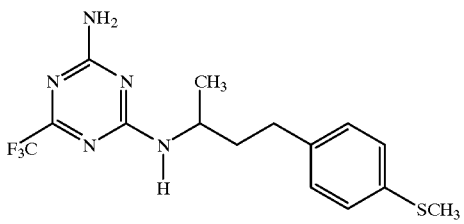

At 20° C. to 30° C., a saturated solution of 6.0 g (0.1 1 mol) of sodium methoxide in methanol is added dropwise with stirring to a mixture of 31.5 g (0.10 mol) of (RIS)-1-(1-methyl-3-(4-methylthio-phenyl)-propyl)-biguanide (racemic), 15.5 g (0.10 mol) of ethyl trifluoroacetate and 150 ml of methanol, and the reaction mixture is then stirred at approximately 20° C. for about 20 hours. The mixture is then diluted to about three times its original volume using methylene chloride, washed with water and then with 1N aqueous sodium hydroxide solution, dried with sodium sulphate and filtered. The solvent is carefully distilled off from the filtrate under water pump vacuum.

This gives 12.1 g (34% of theory) of (R/S)-2-amino-4-(1-methyl-3-(4-methylthio-phenyl)-propylamino)-6-trifluoromethyl-1,3,5-triazine (racemate) as an amorphous residue.

Example (II-2)

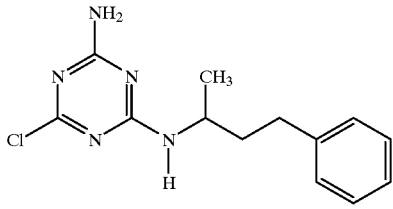

At 20° C. to 30° C., 5.7 mml of a 25% strength aqueous solution of ammonia are added dropwise with stirring to a mixture of 5.4 g (18.2 mmol) of (R/S)-2,4-dichloro-6(1-methyl-3-phenyl-propylamino)-1,3,5-triazine (racemic) and 35 ml of tetrahydrofuran, and the reaction mixture is then stirred at approximately 20° C. for about another 4 hours. The mixture is concentrated under water pump vacuum and the residue is then shaken with ethyl acetate/saturated aqueous sodium chloride solution, the organic phase is separated off and the aqueous phase is re-extracted with ethyl acetate; the organic phases are combined, dried with sodium sulphate and filtered. The filtrate is concentrated under water pump vacuum and the residue is crystallized by digestion with ethyl acetate/hexane. The crystalline product is then isolated by filtration with suction.

This 4.3 g (85% of theory) of (R/S)-2-amino-4chloro-6-(1-methyl-3-phenyl-propyl-amino)-1,3,5-triazine (racemate) of melting point 115° C.

Starting Materials of the Formula (VI)

Example (VI-1)

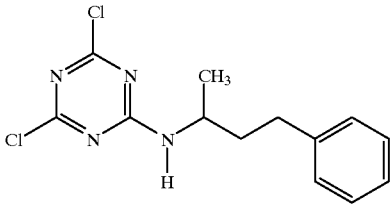

A solution of 16.34 g (0.11 mol) of (R/S)-1-methyl-3-phenyl-propylamine and 14.2 g (0.11 mol) of ethyldiisopropylamine in 20 ml of tetrahydrofuran is added with stirring to a mixture of 20.2 g (0.11 mol) of cyanuric chloride (2,4,6-trichloro-1,3,5-triazine) and 80 ml of tetrahydrofuran which had been cooled to 40° C. to −50° C. The reaction mixture is stirred at the abovementioned temperature for 30 minutes and then at room temperature (about 20° C.) for another 30 minutes. The mixture is concentrated and the residue is then shaken with diethyl ether/saturated aqueous ammonium chloride solution, the organic phase is separated off and the aqueous phase is re-extracted; the combined organic phases are dried with sodium sulphate and filtered. The filtrate is concentrated under water pump vacuum, the residue is digested with petroleum ether/methyl t-butylether and the resulting crystalline product is isolated by filtration with suction.

This gives 27.5 g (84% of theory) of (R/S)-2,4-dichloro-6-(1-methyl-3-phenyl-propylamino)-1,3,5-triazine (racemate) of melting point 79° C.

USE EXAMPLES

Example A

Pre-emergence-test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is watered with the preparation of active compound. The amount of water per unit area is advantageously kept constant. The concentration of active compound in the preparation is immaterial, only the application rate of active compound per unit area matters.

After three weeks, the degree of damage to the plants is scored visually in % damage in comparison to the development of the untreated control.

The figures denote:

0%=no effect (like untreated control)

100%=total destruction

In this test, the compounds of Preparation Examples 1, 8, 27, 28, 53, 54, 56 and 57, for example, show strong activity against weeds, and some of them are tolerated well by crop plants, such as, for example, maize and cotton (cf. Table A). "ai"="active ingredient".

TABLE A

Pre-emergence-test/greenhouse

| Active compound of Preparation Ex. No. | Application rate (g of ai./ha) | Maize | Cotton | Alope-curus | Digi-taria | Sorghum | Ama-ranthus | Cheno-podium | Matri-caria |
|---|---|---|---|---|---|---|---|---|---|
| (1) | 125 | 0 | 0 | 100 | 95 | 100 | 100 | 100 | 100 |

| Active compound of Preparation Ex. No. | Application rate (g of ai./ha) | Maize | Alopecurus | Setaria | Amaranthus |
|---|---|---|---|---|---|
| (54) | 1000 | 20 | 90 | 100 | 80 |

TABLE A-continued

Pre-emergence-test/greenhouse

| Active compound of Preparation Ex. No. | Application rate (g of ai./ha) | Alopecurus | Setaria | Abutilon | Amaranthus | Galium | Sinapis |
|---|---|---|---|---|---|---|---|
| (57) | 1000 | 95 | 90 | 90 | 100 | 100 | 100 |
| (28) | 1000 | 80 | 100 | 100 | 100 | 100 | 100 |

| Active compound of Preparation Ex. No. | Application rate (g of ai./ha) | Alopecurus | Setaria | Amaranthus | Galium | Sinapis |
|---|---|---|---|---|---|---|
| (53) | 1000 | 80 | 100 | 80 | 90 | 100 |

TABLE A-continued

Pre-emergence-test/greenhouse

| Structure | Rate | | | | | |
|---|---|---|---|---|---|---|
| Compound (56) | 1000 | 100 | 90 | 100 | 100 | 100 |

| Active compound of Preparation Ex. No. | Application rate (g of ai./ha) | Alopecurus | Abutilon | Amaranthus | Xanthium |
|---|---|---|---|---|---|
| Compound (8) | 1000 | 70 | 80 | 100 | 80 |

| Active compound of Preparation Ex. No. | Application rate (g of ai./ha) | Setaria | Abutilon | Amaranthus | Galium |
|---|---|---|---|---|---|
| Compound (27) | 1000 | 100 | 70 | 100 | 100 |

Example B

Post-emergence-test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound such that the particular amounts of active compounds desired are applied per unit area. The concentration of the spray liquor is chosen so that the particular amounts of active compound desired are applied in 1000 l of water/ha.

After three weeks, the degree of damage to the plants is scored visually in % damage in comparison to the untreated control.

The figures denote:

0%=no effect (like untreated control)

100%=total destruction

In this test, the compounds of Preparation Examples 1, 9, 28, 29, 32, 56, 67 and 70, for example, show strong activity against weeds, and some of them are tolerated well by crop plants, such as, for example, maize and wheat (cf. Table B).

TABLE B

| Post-emergence test/greenhouse | | | | | | |
|---|---|---|---|---|---|---|
| Active compound of Preparation Ex. No. | Application rate (g of ai./ha) | Wheat | Amaranthus | Chenopodium | Datura | Solanum |
| 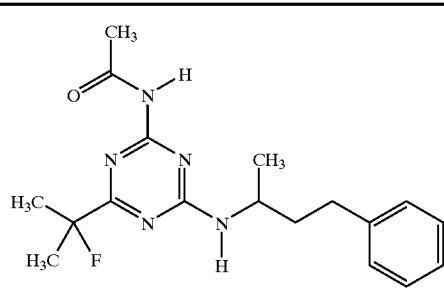 (1) | 125 | 10 | 95 | 95 | 100 | 95 |
| Active compound of Preparation Ex. No. | Application rate (g of ai./ha) | Maize | Avena fatua | Setaria | Abutilon | Amaranthus | Xanthium |
| 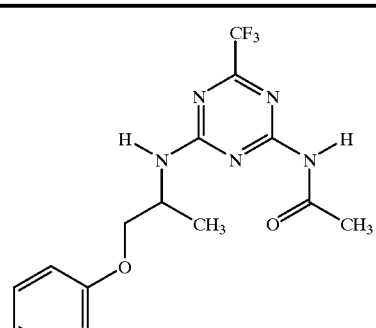 (9) | 1000 | 10 | 100 | 100 | 100 | 100 | 100 |
| 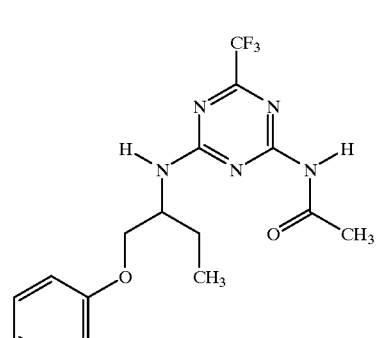 (32) | 1000 | 20 | 70 | 100 | 100 | 100 | 80 |

TABLE B-continued

Post-emergence test/greenhouse

| Active compound of Preparation Ex. No. | Application rate (g of ai./ha) | Setaria | Abutilon | Amaranthus | Galium | Xanthium |
|---|---|---|---|---|---|---|
| (29) | 1000 | 90 | 100 | 100 | 100 | 100 |
| (67) | 1000 | 100 | 100 | 100 | 100 | 100 |
| (28) | 1000 | 90 | 100 | 100 | 100 | — |

TABLE B-continued

Post-emergence test/greenhouse

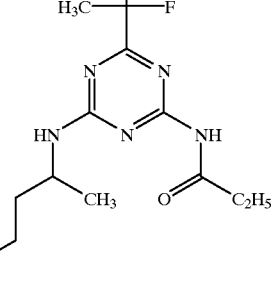

| | 1000 | 100 | 100 | 100 | 100 | 100 |

(70)

| Active compound of Preparation Ex. No. | Application rate (g of ai./ha) | Alopecurus | Avena fatua | Amaranthus | Sinapis |
|---|---|---|---|---|---|
| | 1000 | 70 | 90 | 70 | 100 |

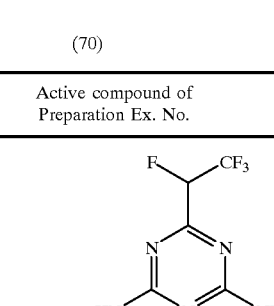

(56)

What is claimed is:

1. A substituted 2,4-diamino-1,3,5-triazine of the formula (I), $$\text{(I)}$$

wherein
- $R^1$ represents hydrogen, an unsubstituted alkyl group having 1 to 6 carbon atoms or a cyano-, halogen- or $C_1$–$C_4$-alkoxy-substituted alkyl having 1 to 6 carbon atoms,
- $R^2$ represents formyl; an unsubstituted alkylcarbonyl, alkoxycarbonyl or alkylsulphonyl having in each case 1 to 6 carbon atoms in the alkyl group: a cyano-, halogen- or $C_1$–$C_4$-alkoxy-substituted alkylcarbonyl, alkoxycarbonyl or alkylsulphonyl having in each case 1 to 6 carbon atoms in the alkyl group; an unsubstituted phenylcarbonyl. napthylcarbonyl, phenylsulphonyl or naphthylsulphonyl; a cyano-, halogen-, $C_1$–$C_4$-alkyl-, halogeno-$C_1$–C-alkyl-, $C_1$–$C$,-alkoxy-, halogeno-$C_1$–$C_4$-alkoxy- or $C_1$–$C_4$-alkoxy-carbonyl-substituted phenylcarbonyl, napthylcarbonyl, phenylsulphonyl or naphthylsulphonyl:
- $R^3$ represents an unsubstituted alkyl having 1 to 6 carbon atoms: an unsubstituted cycloalkyl having 3 to 6 carbon atoms; an hydroxyl-, cyano-, halogen- or $C_1$–$C_4$-alkoxy-substituted alkyl having 1 to 6 carbon atoms; a cyano-, halogen- or $C_1$–$C_4$-alkyl-substituted cycloalkyl having 3 to 6 carbon atoms,
- $R^4$ represents hydrogen or an alkyl group having 1 to 4 carbon atoms,
- A represents oxygen or methylene, provided that if Ar represents an optionally substituted phenyl or naphthyl, A cannot represent methylene,
- Ar represents an optionally substituted phenyl, naphthyl or heterocyclyl, where the heterocyclyl radicals are selected from the group consisting of:
  furyl, benzofuryl, dihydrobenzofuryl, tetrahydrofuryl, thienyl, benzothienyl, thiazolyl, benzothiazolyl, oxazolyl, benzoxazolyl, thiadiazolyl, oxadiazolyl, pyrazolyl, pyrrolyl, indolyl, pyridinyl, quinolinyl, isoquinolinyl and pyrimidinyl, and wherein the possible substituents are selected from the group consisting of:

hydroxyl; cyano; nitro; halogen; unsubstituted alkyl or alkoxy having in each case 1 to 6 carbon atoms in the alkyl group unsubstituted alkylcarbonyl, alkoxycarbonyl, alkylthio, alkylsulphinyl or alkylsulphonyl having in each case 1 to 6 carbon atoms in the alkyl group; an hydroxy-, cyano- or halogen-substituted alkyl or alkoxy having in each case 1 to 6 carbon atoms; a halogen-substituted alkylcarbonyl, alkoxycarbonyl, alkylthio, alkylsulphinyl or alkylsulphonyl having in each case 1 to 6 carbon atoms in the alkyl groups; an unsubstituted phenyl or phenoxy: an hydroxyl-, cyano-, nitro-, halogen-, $C_1$–$C_4$-alkyl, $C_1$–$C_4$-halogenoalkyl-, $C_1$–$C_4$-alkoxy- or $C_1$–$C_4$-halogenoalkoxy-substituted phenyl or phenoxy; an unsubstituted methylenedioxy or ethylenedioxy: and a halogen-substituted methylenedioxy or ethylenedioxy; and Z is selected from the group consisting of hydrogen; an unsubstituted alkyl, alkylcarbonyl, alkoxycarbonyl, alkylsulphinyl or alkylsulphonyl having in each case 1 to 6 carbon atoms in the alkyl group: an hydroxyl-, cyano-, nitro-, halogen-. $C_1$–$C_4$-alkoxy-, $C_1$–$C_{14}$-alkylcarbonyl-, $C_1$–$C_4$-alkoxycarbonyl-, $C_1$–$C_4$-alkylthio-, $C_1$–$C_4$-alkylsulphinyl- or $C_1$–$C_4$ alkylsulphonyl-substituted alkyl, alkylcarbonyl, alkoxycarbonyl, alkylsulphinyl or alkylsulphonyl having in each case 1 to 6 carbon atoms in the alkyl group; and an unsubstituted alkenyl or alkinyl having in each case 2 to 6 carbon atoms; and a halogen- or $C_1$–$C_4$-alkoxy-substituted alkenyl or alkinyl having in each case 2 to 6 carbon atoms.

2. The substituted triazine of claim 1 wherein $R^1$ represents hydrogen; an unsubstituted methyl, ethyl, n- or i-propyl, n-, i-, s- or t-butyl; or an hydroxyl-, cyano-, fluorine-, chlorine-, methoxy- or ethoxy-substituted methyl, ethyl, n- or i-propyl, n-, i-, s- or t-butyl;

$R^2$ represents an unsubstituted acetyl, propionyl, n- or i-butyroyl, methoxycarbonyl, ethoxycarbonyl, methylsulphonyl, ethylsulphonyl, n- or i-propylsulphonyl, n-, i-, s- or t-butylsulphonyl; a cyano-, fluorine-, chlorine-, bromine-, methoxy- or ethoxy-substituted acetyl, propionyl, n- or i-butyroyl, methoxycarbonyl, ethoxycarbonyl, methylsulphonyl, ethylsulphonyl, n- or i-propylsulphonyl, n-, i-, s- or t-butylsulphonyl; an unsubstituted phenylcarbonyl or phenylsulphonyl; or a cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-, methoxycarbonyl- or ethoxycarbonyl-substituted phenylcarbonyl or phenylsulphonyl;

$R^3$ represents an unsubstituted methyl, ethyl, n- or i-propyl, n-, i-, s- or t-butyl; an hydroxyl-, cyano-, fluorine-, chlorine-, methoxy- or ethoxy-substituted methyl, ethyl, n- or i-propyl, n-, i-, S- or t-butyl; an unsubstituted cyclopropyl, cyclobutyl, cyclopentyl or cyclohexyl; or a cyano-, fluorine-, chlorine-, methyl- or ethyl-substituted cyclopropyl, cyclobutyl, cyclopentyl or cyclohexyl;

$R^4$ represents hydrogen or methyl,

A represents oxygen or methylene,

Ar represents in each case optionally substituted phenyl, naphthyl or heterocyclyl, where the heterocyclyl radicals are selected from the group selected from the group consisting of:

furyl, benzofuryl, dihydrobenzofuryl, tetrahydrofuryl, thienyl, benzothienyl, thiazolyl, benzothiazolyl, oxazolyl, benzoxazolyl, thiadiazolyl, oxadiazolyl, pyrazolyl, pyrrolyl, indolyl, pyridinyl, quinolinyl, isoquinolinyl and pyrimidinyl, and wherein the possible substituents are selected from the group consisting of:

hydroxy; cyano; nitro; fluorine; chlorine; bromine; unsubstituted methyl, ethyl, n- or i-propyl, n-, i-, s- or t-butyl, methoxy, ethoxy, n- or i-propoxy, n-, i-, s- or t-butoxy; an hydroxyl-cyano-, fluorine- or chlorine-substituted methyl, ethyl, n- or i-propyl, n-, i-, s- or t-butyl, methoxy, ethoxy, n- or i-propoxy, n-, i-, s- or t-butoxy; unsubstituted acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl; a fluorine- or chlorine-substituted acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl; an unsubstituted substituted phenyl or phenoxy; an hydroxyl-, cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl or phenoxy; unsubstituted methylenedioxy or ethylenedioxy; or a fluorine- or chlorine-substituted methylenedioxy or ethylenedioxy, and Z represents hydrogen; an unsubstituted methyl, ethyl, n- or i-propyl, n-, i-, s- or t-butyl, methylsulphinyl, ethylsulphinyl, n- or i-propylsulphinyl, methylsulphonyl, ethylsulphonyl, n- or i-propylsulphonyl; an hydroxyl-, cyano-, nitro-, fluorine-, chlorine, methoxy-, ethoxy-, n- or i-propoxy-, n-, i-, s- or t-butoxy-, methylthio-ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methylsulphinyl, ethylsulphinyl, n- or i-propylsulphinyl, methylsulphonyl, ethylsulphonyl, n- or i-propylsulphonyl; an unsubstituted ethenyl, propenyl, butenyl, ethinyl, propinyl or butinyl; or a fluorine-, chlorine-, bromine-, methoxy- or ethoxy-substituted ethenyl, propenyl, butenyl, ethinyl, propinyl or butinyl.

3. A herbicidal composition comprising one or more compounds according to claim 1 and one or more inert carriers.

4. A method of controlling weeds comprising applying an effective amount of a compound of claim 1 to weeds or their habitat.

* * * * *